(12) United States Patent
Honda et al.

(10) Patent No.: US 7,049,350 B2
(45) Date of Patent: May 23, 2006

(54) POLYMERIZABLE COMPOUND, POLYMERIZABLE COMPOSITION AND CURED PRODUCT CONTAINING THE COMPOUND

(75) Inventors: Yoshihiro Honda, Oita (JP); Keisuke Ohta, Oita (JP); Kazuhiko Ooga, Oita (JP); Kazufumi Kai, Oita (JP); Hiroshi Uchida, Oita (JP)

(73) Assignee: Showa Denko K.K., Tokyo (JP)

( * ) Notice: Subject to any disclaimer, the term of this patent is extended or adjusted under 35 U.S.C. 154(b) by 43 days.

(21) Appl. No.: 10/484,877

(22) PCT Filed: Jul. 25, 2002

(86) PCT No.: PCT/JP02/07569

§ 371 (c)(1),
(2), (4) Date: Jan. 27, 2004

(87) PCT Pub. No.: WO03/010124

PCT Pub. Date: Feb. 6, 2003

(65) Prior Publication Data

US 2004/0235980 A1 Nov. 25, 2004

Related U.S. Application Data

(60) Provisional application No. 60/308,862, filed on Aug. 1, 2001.

(30) Foreign Application Priority Data

| Jul. 27, 2001 | (JP) | ............................. 2001-226909 |
| Nov. 20, 2001 | (JP) | ............................. 2001-354305 |
| Jun. 28, 2002 | (JP) | ............................. 2002-189063 |

(51) Int. Cl.
*C08F 2/46* (2006.01)
*C07C 69/60* (2006.01)

(52) U.S. Cl. ........................ 522/182; 522/100; 522/101; 522/103; 522/104; 522/173; 522/181

(58) Field of Classification Search ................ 522/104, 522/100, 101, 103, 113, 120, 121, 122, 123, 522/181, 182, 165, 166, 168, 169, 170, 173
See application file for complete search history.

(56) References Cited

U.S. PATENT DOCUMENTS 2,514,786 A 7/1950 Croxall et al

FOREIGN PATENT DOCUMENTS

| JP | 08-184961 | * | 7/1996 |
| RU | 1155584 | * | 5/1985 |
| RU | 1178755 A | * | 9/1985 |

OTHER PUBLICATIONS

Matyni et al: "Synthesis and Characterization of the Epoxyfumarate Resins" Journal of Applied Polymer Science, vol. 84, 716-722 (2002).*

Jiri Klaban Jaroslav Vlcek et al: "Studium Der Polymerisation Von Bis (Glycerinmonoallylaether) Fumarat Mittels Infrarot Spektroskopie" Journal of Polymer Science, Polymer Symposia, John Wiley and Sons. New York, US, No. 16, 1967, pp. 247-256.

* cited by examiner

*Primary Examiner*—James J. Seidleck
*Assistant Examiner*—Sanza L. McClendon
(74) *Attorney, Agent, or Firm*—Sughrue Mion, PLLC

(57) ABSTRACT

A polymerizable compound represented by formula (1): wherein each $R^1$ independently represents at least one organic residue selected from the group consisting of alkylene groups, branched alkylene groups, cycloalkylene groups and arylene groups, $R^2$ represents an organic residue derived from an alcohol compound, a phenol compound or a carboxylic acid compound, n represents an integer of 0 to 20, a production process of the polymerizable composition, a composition using the polymerizable compound, a cured product obtained by curing the composition and a production process of the cured product. The polymerizable compound exhibits a good adhesive property to a substrate such as glass and is imparted with radical polymerizability to enable heat curing and/or active energy ray curing.

(1)

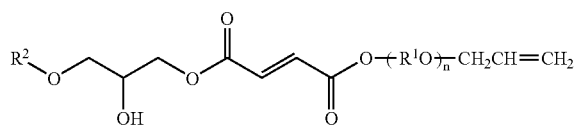

17 Claims, 8 Drawing Sheets

POLYMERIZABLE COMPOUND, POLYMERIZABLE COMPOSITION AND CURED PRODUCT CONTAINING THE COMPOUND

CROSS-REFERENCE TO RELATED APPLICATION

This application is an application filed under 35 U.S.C. § 111(a) claiming benefit pursuant to 35 U.S.C. § 119(e)(1) of the filing date of the Provisional Application 60/308,862 filed Aug. 1, 2001, pursuant to 35 U.S.C. § 111(b).

TECHNICAL FIELD

The present invention relates to novel polymerizable compounds, a production process of the polymerizable compounds, polymerizable compositions containing the polymerizable compounds, cured products obtained by curing the polymerizable compositions, and a production process of the cured products.

More specifically, the present invention relates to polymerizable compounds of exhibiting good adhesive property to a substrate such as of polyethylene terephthalate (PET) and exhibiting radical polymerizability to enable heat curing and/or curing by an active energy ray, and also relates to a production process of the polymerizable compounds, polymerizable compositions containing the polymerizable compounds, and cured products obtained by curing the polymerizable compositions.

The term "active energy ray" as used herein means an electromagnetic wave or corpuscular rays having energy, such as near-infrared rays, visible rays, ultraviolet rays, vacuum ultraviolet rays, Xrays, γ rays and an electron beam.

Also, the term "heat curing" as used herein means to perform curing, using radical polymerization, by heat.

BACKGROUND ART

Representative radical curable resins having hydroxyl groups may include, for example, vinyl ester resins (epoxy acrylates) obtained by reacting an epoxy resin with acrylic acid, methacrylic acid or the like. The vinyl ester resins have (meth)acrylate groups having radical polymerizability and thus can be heat cured or light cured. Therefore, they are broadly used as resins for UV offset printing ink or resins for synthetic marble.

However, the vinyl ester resins suffer from polymerization inhibition by oxygen during polymerization. Therefore, they may suffer insufficient curing when used in a thin film coating process such as for obtaining a thin coating.

For avoiding the polymerization inhibition of vinyl ester resins by oxygen, it has been proposed to introduce an allyl ether group. Specifically, for example, Japanese Unexamined Patent Publication No. 61-101518 (JP-A-61-101518) may be mentioned. However, by the technique of JP-A-61-101518, the copolymerizability of a (meth)acrylate group and an allyl ether group is not necessarily good, and when this technique is employed in a thin film coating process such as for obtaining a thin coating, the polymerization rate is not necessarily sufficient and insufficient curing may result.

Further, as radical curable resins other than the vinyl ester resins, there are commercially available ester compounds of a polyhydric alcohol such as trimethylolpropane di-(meth)acrylate or pentaerythritol tri-(math)acrylate and (meth)acrylic acid, containing partially retained hydroxyl groups.

However, these compounds also suffer from polymerization inhibition by oxygen during polymerization and therefore, may suffer insufficient curing when used in a thin film coating process such as for obtaining a thin coating.

Epoxy resins are excellent resins having extensive uses for coating materials, electrical insulating materials, laminate structure materials, civil engineering and construction materials, adhesives and the like. In particularly, it is known that they have a good adhesion as coating materials. However, they have problems in that a long time is necessary for curing and an amine used as a curing agent is retained in a large amount so as to cause coloration of the cured products.

In order to solve these problems, it has been proposed to modify the epoxy resins, but other problems have arisen, as described above with respect to JP-A-61-101518. Therefore, polymerizable compounds having an improved polymerizability and a polymerizable composition containing such a polymerizable compound have been required.

In general, the epoxy resin is acknowledged to be "a generic term for compounds having two or more epoxy groups (oxylane ring) within one molecule" (see, "24 Epoxy Resin" of *Engineering Plastic Jiten* (*Dictionary of Engineering Plastics*), 1st ed., 1st imp., page 621, Gihodo (Dec. 15, 1988)). A representative epoxy resin shown here is a bisphenol A-diglycidyl ether produced by the condensation of bisphenol A and epichlorohydrin. Other than this, those having a relatively low molecular weight, where a glycidyl group is added to the terminal hydroxyl group of (poly) ethylene glycol or where a glycidyl group is added to the hydroxyl group of 1,6-hexanediol, are described as examples of the epoxy resin.

On the other hand, compounds having one epoxy group within one molecule, such as allyl glycidyl ether, phenyl glycidyl ether and cresol glycidyl ether (specifically, for example, ADEKAGLYCIDOL ED-529 (produced by Asahi Denka Kogyo K.K.)), are commercially available as diluents for the epoxy resin. In "24 Epoxy Resin, 1.2 Curing Reaction (2) Auxiliary Material" of *Dictionary of Engineering Plastics,* supra, page 635, it is stated that "Some of these reactive diluents are previously mixed with an epoxy resin and the mixture is commercially available as one grade of epoxy resin".

Accordingly, in the present invention, the epoxy resin is defined as "a compound having at least one epoxy group" and not limited in the size of the molecular weight.

DISCLOSURE OF INVENTION

It is an object of the present invention to solve the above-described problems and provide a novel polymerizable compound capable of exhibiting good adhesive property to a substrate such as of PET and capable of being heat cured and/or cured by an active energy ray without being subject to polymerization inhibition by oxygen. It is another object of the present invention to provide a production process of the polymerizable compound, a composition using the polymerizable compound, a cured product obtained by curing the composition, and a production process of the cured product.

As a result of extensive investigations to solve the above-described problems, the present inventors have found that a polymerizable compound produced by the reaction of an epoxy compound, particularly an epoxy resin with a fumaric acid monoester having an allyl group and optionally a (meth)acrylic acid can provide a cured product of exhibiting good adhesive property to a substrate such as of PET and capable of heat curing and/or curing by an active energy ray without being subject to polymerization inhibition by oxygen. The present invention has been accomplished based on this finding.

More specifically, the present invention (I) provides a polymerizable compound represented by the following formula (1):

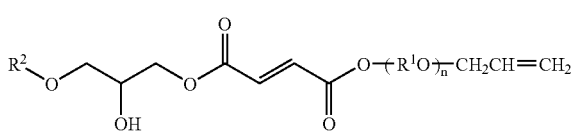
(1)

wherein each $R^1$ independently represents at least one organic residue selected from the group consisting of alkylene groups, branched alkylene groups, cycloalkylene groups and arylene groups, $R^2$ represents an organic residue derived from an alcohol compound, a phenol compound or a carboxylic acid compound, n represents an integer of 0 to 20, and $R^2$ may further contain a group represented by the following formula (2) and/or formula (3):

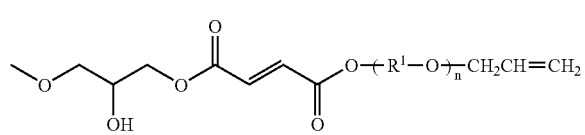
(2)

wherein $R^1$ and n are as defined above.

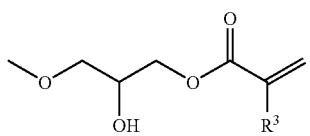
(3)

wherein $R^3$ represents H or $CH_3$.

The term "polymerizable compound" as used herein may be referred to as a "modified epoxy resin" where a compound included in the "epoxy resin" defined above is used for a part or all of the starting material therefor. For example, a vinyl ester resin (epoxy acrylate) and the like obtained by performing an addition reaction of an acrylic acid to an epoxy resin and thereby imparting radical polymerizability are also included in the "modified epoxy resin".

The term "(meth)arylic acid" as used herein refers to acrylic acid and methacrylic acid.

The present invention (II) provides a process for producing the polymerizable compound of the present invention (I), comprising:

a step of performing an addition reaction between at least one compound selected from the compounds represented by the following formula (4) and at least one compound selected from the compounds represented by the following formula (5) in the presence of a catalyst to obtain a polymerizable compound:

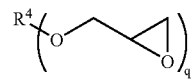
(4)

wherein $R^4$ represents an organic residue derived from an alcohol compound, a phenol compound or a carboxylic acid compound, and q represents an integer of 1 or more;

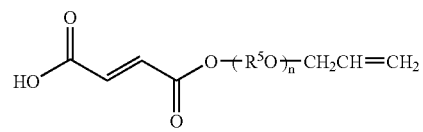
(5)

wherein $R^5$ represents at least one member selected from an alkylene group, a branched alkylene group, a cycloalkylene group and an arylene group, and n represents an integer of 0 to 20.

The present invention (III) provides a polymerizable composition comprising at least one polymerizable compound of the present invention (I) as an essential component.

The present invention (IV) provides the polymerizable composition of the present invention (III), which contains from 0.1 to 10 parts by mass of at least one radical polymerization initiator per 100 parts by mass of all curable components in the polymerizable composition.

The present invention (V) provides a cured product obtained by curing the polymerizable composition of the present invention (III) or the present invention (IV), and a production process of the cured product.

BEST MODE FOR CARRYING OUT THE INVENTION

Figure 1:
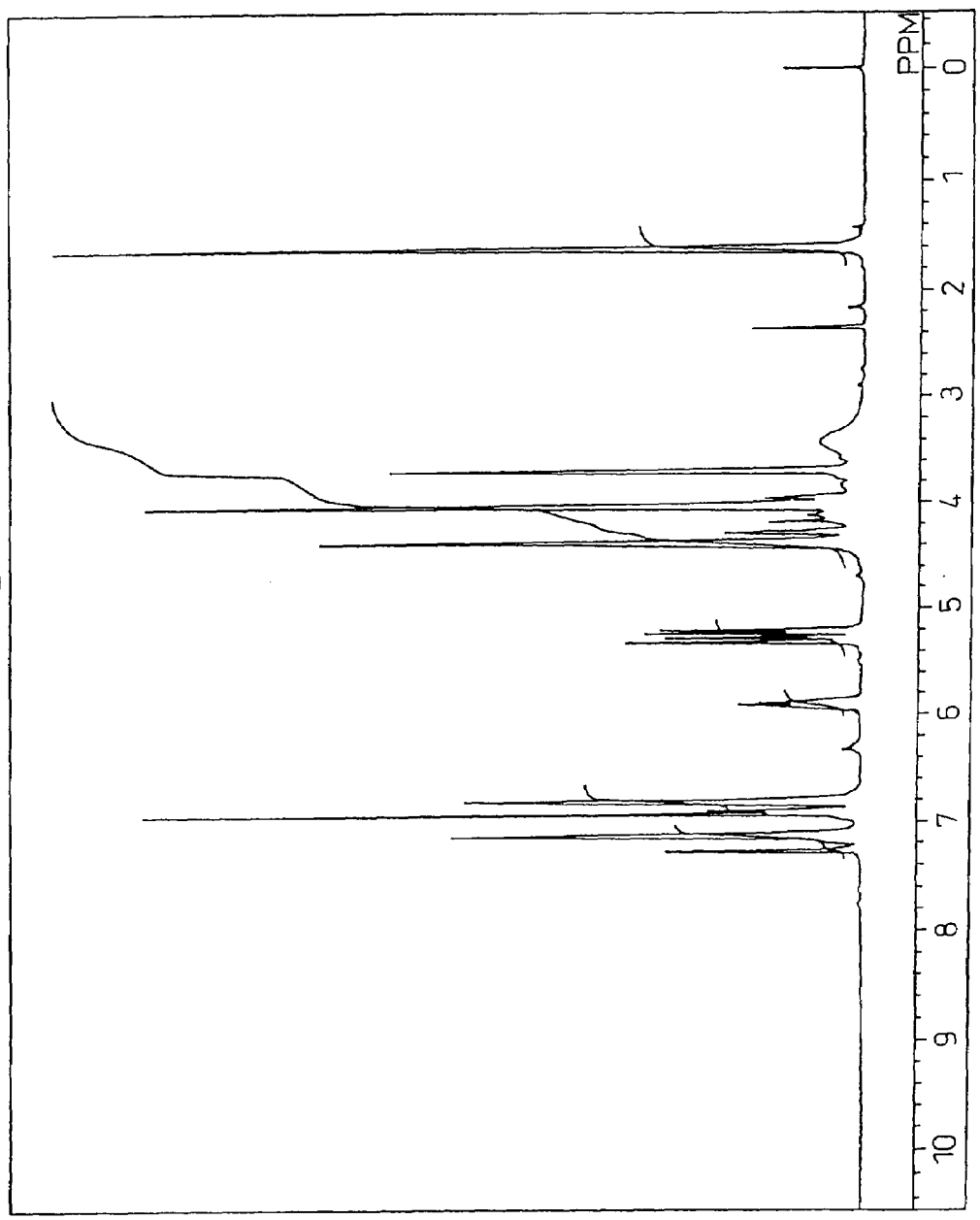
FIG. 1 is a $^1$H-NMR spectrum chart of the polymerizable compound obtained in Example 1.

The present invention is described in detail below.

The present invention (I) is a polymerizable compound represented by the above formula (1).

In formulae (1) and (2), each $R^1$ independently represents at least one organic residue selected from the group consisting of alkylene groups, branched alkylene groups, cycloalkylene groups and arylene groups.

Specific examples of $R^1$ in formulae (1) and (2) include a linear alkylene group such as a methylene group, an ethylene group, a propylene group, a butylene group, a pentylene group, a hexylene group, a heptylene group, an octylene group, a nonylene group and a decylene group; a cycloalkylene group such as a cyclopropylene group, a cyclobutylene group, a cyclopentylene group, a cyclohexylene group, a cycloheptylene group, a cyclooctylene group, a dicyclopentylene group and a tricyclopentylene group; a branched alkylene group such as a methylethylene group, a phenylethylene group and a 1,2-diphenylethylene group; an alkylene group such as a phenylethylene group and a 1,2-diphenylethylene group; and an arylene group such as a phenylene group, a naphthylene group and an anthranylene group.

Among these, in view of easy availability of raw material and ease of synthesis, preferred as $R^1$ in formulae (1) and (2) are the following structural formulae (6) to (12):

(6)

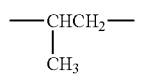
(7)

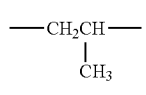
(8)

(9)

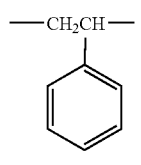
(10)

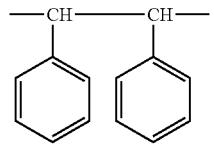
(11)

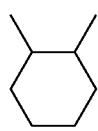
(12)

In formulae (1) and (2), the term "each $R^1$ independently represents" means that all $R^1$s in the polymerizable compound of the present invention (I) may have different structures from each other or may have the same structure. In other words, it may be possible that all of $R^1$s have the same structure, or some of $R^1$s have the same structure and the remaining $R^1$s have different structures.

In formula (1), $R^2$ represents an organic residue derived from an alcohol compound, a phenol compound or a carboxylic acid compound. $R^2$ may further contain a group represented by formula (2) or formula (3).

The term "$R^2$ represents an organic residue derived from an alcohol compound, a phenol compound and a carboxylic acid compound" means not only the case where $R^2$ is an organic residue derived only from an alcohol compound, a phenol compound and a carboxylic acid compound but also the case where $R^2$ is a group which contains an organic residue derived from an alcohol compound, a phenol compound and a carboxylic acid compound, and thus $R^2$ may contain an organic residue derived from a sulfide or the like in addition to the organic residue derived from an alcohol compound, a phenol compound and a carboxylic acid compound.

Examples of the "alcohol compound" include monool compounds such as methanol, ethanol, propanol, isopropanol, 1-butanol, 2-butanol and t-butanol; diol compounds such as ethylene glycol, diethylene glycol, triethylene glycol, tetraethylene glycol, propylene glycol, dipropylene glycol, tripropylene glycol, tetraethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, neopentyl glycol, 1,2-cyclohexanediol, 1,3-cyclohexanediol, 1,4-cyclohexanediol, 1,1-cyclohexanedimethanol, 1,2-cychohexanedimethanol, 1,3-cyclohexanedimethanol, 1,4-cyclohexanedimethanol, hydrogenated bisphenol A, tricyclo[5.2.1.0$^{2.6}$]decanedimethanol, bisphenol A ethylene oxide adduct and bisphenol A propylene oxide adduct; triol compounds such as glycerin, trimethylolpropane and trimethylolethane; and tetraol compounds such as pentaerythritol and diglycerin. However, the alcohol compound is of course not limited to these specific examples.

Examples of the "phenol compound" include phenol, catechol, resorcinol, hydroquinone, bisphenol A, brominated bisphenol A, bisphenol F, phenol novolak resin and cresol novolak resin. However, the phenol compound is of course not limited to these specific examples.

Examples of the "carboxylic acid compound" include acetic acid, propionic acid, butyric acid, benzoic acid, maleic acid, maleic anhydride, fumaric acid, 1,2-cyclohexanedicarboxylic acid, 1,2-cyclohexanedicarboxylic anhydride, 1,3-cyclo-hexanedicarboxylic acid, 1,4-cyclohexanedicarboxylic acid, 3-cyclohexene-1,2-dicarboxylic acid, 4-methyl-4-cyclo-hexene-1,2-dicarboxylic acid, phthalic acid, phthalic anhydride, isophthalic acid, terephthalic acid, 2,6-naphthalenedicarboxylic acid, 1,2,3-benzenetricarboxylic acid, 1,2,4-benzenetricarboxylic acid and 1,3,5-benzenetricarboxylic acid. However, the carboxylic acid compound is of course not limited to these specific examples.

Particularly, in view of easy availability, the organic residue contained in $R^2$ is preferably an organic residue derived from ethylene glycol, propylene glycol, 1,3-propanediol, 1,4-butanediol, 1,6-hexanediol, neopentyl glycol, glycerin, trimethylolethane, trimethylolpropane, 1,4-cyclohexanediol, 1,4-cyclohexanedimethanol, bisphenol A, bisphenol A propylene oxide adduct, bisphenol A ethylene oxide adduct, brominated bisphenol A, hydrogenated bisphenol A, bisphenol F, phenol novolak resin, cresol novolak resin, 1,2-cyclohexanedicarboxylic acid, 1,3-cyclohexanedicarboxylic acid, 1,4-cyclohexanedicarboxylic acid, 3-cyclohexene-1,2-dicarboxylic acid, phthalic acid, isophthalic acid and terephthalic acid.

The combination of $R^1$ in formulae (1) and (2) and $R^2$ in formula (1) is preferably such that $R^1$ is at least one organic residue selected from a methylene group, an ethylene group, a propylene group, a butylene group, a hexylene group, an octylene group, a cyclopentylene group, a cyclohexylene group, a dicyclopentylene group, a methylethylene group, a phenylethylene group, a 1,2-diphenylethylene group, a phenylene group and a naphthylene group, and $R^2$ is an organic residue derived from at least one compound selected from ethylene glycol, diethylene glycol, triethylene glycol, tetraethylene glycol, propylene glycol, dipropylene glycol, tripropylene glycol, tetraethylene glycol, 1,4-butanediol, 1,6-hexanediol, 1,8-octanediol, neopentyl glycol, 1,2-cyclohexanediol, 1,3-cyclohexanediol, 1,4-cyclohexanediol, 1,4-cyclohexanedimethanol, hydrogenated bisphenol A, tricyclo-[5.2.1.0$^{2.6}$]decanedimethanol, bisphenol A ethylene oxide adduct, bisphenol A propylene oxide adduct, glycerin, trimethylolpropane, trimethylolethane, pentaerythritol, diglycerin, catechol, bisphenol A, brominated bisphenol A, bisphenol F, phenol novolak resin, cresol novolak resin, maleic acid, maleic anhydride, fumaric acid, 1,2-cyclohexanedicarboxylic acid, 1,2-cyclohexanedicarboxylic anhydride, 1,3-cyclo-hexanedicarboxylic acid, 1,4-cyclohexanedicarboxylic acid, 3-cyclohexene-1,2-dicarboxylic acid, 4-methyl-4-cyclohexene-1,2-dicarboxylic acid, phthalic acid, phthalic anhydride, isophthalic acid and terephthalic acid.

Among these, in view of easy availability of raw materials and ease of synthesis, preferred is a combination where $R^1$ is at least one organic residue selected from the above formulae (6) to (12) and $R^2$ is an organic residue derived from at least one compound selected from ethylene glycol, propylene glycol, 1,3-propanediol, 1,4-butanediol, 1,6-hexanediol, neopentyl glycol, glycerin, trimethylolethane, trimethylolpropane, 1,4-cyclohexanediol, 1,4-cyclohexanedimethanol, bisphenol A, bisphenol A propylene oxide adduct, bisphenol A ethylene oxide adduct, brominated bisphenol A, hydrogenated bisphenol A, bisphenol F, phenol novolak resin, cresol novolak resin, 1,2-cyclohexanedicarboxylic acid, 1,3-cyclohexanedicarboxylic acid, 1,4-cyclohexanedicarboxylic acid, 3-cyclohexene-1,2-dicarboxylic acid, phthalic acid, isophthalic acid and terephthalic acid.

In formula (1), n represents an integer of 0 to 20. If n is 21 or more, the molecular weight becomes large and the number of polymerization positions per mass decreases, as a result, the polymerization is disadvantageously liable to proceed incompletely and the cured product obtained may fail to have a sufficiently high hardness.

When n=0, the polymerizable compound of the present invention (I) contains an allyl ester group but this resin is slightly inferior in the radical polymerizability as compared with the case of n=1 or more, namely, containing an allyl ether group. Therefore, n is preferably 1 or more.

$R^2$ in formula (1) may further contain a group of formula (2) and/or formula (3).

$R^1$ and n in formula (2) are as defined above.

$R^3$ in formula (3) is H or $CH_3$. Where $R^3$ is H, the polymerizable compound of the present invention (1) has an acryloyl group. Where $R^3$ is $CH_3$, the polymerizable compound of the present invention (I) has a methacryloyl group. The purpose of the introduction of an acryloyl or methacryloyl group into the polymerizable compound of the present invention (I) is to increase the curing rate of the resulting compound, and this is a highly effective means as a means for increasing the curing rate. However, where the compound belongs to the category of the present invention (I) and has already a sufficiently high curing rate, it is not always necessary to introduce an acryloyl or methacryloyl group.

If the construction of formula (2) is substituted by the construction of formula (3) to too large an extent, the resulting compound may disadvantageously be subject to polymerization inhibition by oxygen. The ratio of the number of the groups represented by formula (3) to the number of the groups represented by formula (2) contained in the polymerizable compound of the present invention (I) is preferably 0 to 10, more preferably 0 to 5, particularly 0 to 2.

Where the polymerizable compound of the present invention (I) contains a plurality of the group of formula (3) in one molecule, all of $R^3$s contained in one molecule may be H, a part of $R^3$s contained in one molecule may be H and the remaining may be $CH_3$, or all of $R^3$s contained in one molecule may be $CH_3$.

The polymerizable compound of the present invention (I) is sufficient if it contains at least one group represented by formula (1) within one molecule. Accordingly, it is not necessary that all epoxy groups present in the raw material epoxy compound are converted into the group represented by formula (1). There is no problem even if an epoxy group partially remains.

For example, when bisphenol A-diglycidyl ether is used as the epoxy compound, it may be possible that two epoxy rings both are converted into the group represented by formula (1), or one is converted into the group represented by formula (1) and another epoxy ring remains as it is.

Particularly, in the case of an epoxy resin derived from a compound having a large number of hydroxyl groups within one molecule, such as phenol novolak resin, it may be possible that all epoxy rings are converted into the group represented by formula (1), or a part are converted into the group represented by formula (1) and the remaining are an epoxy ring as it is. Furthermore, the epoxy resin as a whole may be in the state where these two cases are mixed.

The present invention (II) is described in detail below.

The present invention (II) relates to a process for producing the polymerizable compound of the present invention (I), comprising:

a step of performing an addition reaction between at least one compound selected from the compounds represented by the above formula (4) and at least one compound selected from the compounds represented by the above formula (5) in the presence of a catalyst to obtain a modified epoxy resin.

In the process of the present invention (II), a catalyst is generally used so as to accelerate the reaction.

The catalyst for use in the process of the present invention (II) is not particularly limited insofar as it is a catalyst generally used in the addition reaction of an epoxy and a carboxylic acid. Specific examples of the catalyst may include metal halides such as aluminum chloride, tin chloride and zinc chloride; pyridine compounds such as pyridine, α-picoline, isoquinoline, quinoline, 2-vinylpyridine, 3-vinylpyridine and 4-vinylpyridine; pyridinium salts such as N-methylpyridinium chloride, N-methylpyridinium bromide, N-ethylpyridinium chloride, N-ethylpyridinium bromide, 2-vinylpyridinium chloride, 2-vinylpyridinium bromide, 3-vinylpyridinium chloride, 3-vinylpyridinium bromide, 4-vinylpyridinium chloride and 4-vinylpyridinium bromide; tertiary amines such as N,N-benzyldimethylamine, N,N-dimethylphenylamine, N,N-dimethylcyclohexylamine, 2,4,6-tris(dimethylaminomethyl)-phenol, triethylamine, tri-n-butylamine, N-methylmorpholine, N-ethylmorpholine, N,N-dimethylaniline, N,N-dimethylaminoethyl methacrylate, N,N-dimethylaminoethyl acrylate, N-(3-N',N'-dimethylaminopropyl)-acrylamide and N-(3-N',N'-dimethylaminopropyl)-methacrylamide; quaternary ammonium salts such as benzyltrimethylammonium chloride, benzyltrimethylammonium bromide, benzyltriethylammonium chloride, benzyltriethylammonium bromide, trimethylmethacryloyloxyethylammonium chloride, trimethylmethacryloyloxyethylammonium bromide, trimethylacryloyloxyethylammonium chloride, trimethylacryloyloxyethylammonium bromide, trimethylacryloy laminopropylammonium chloride, trimethylacryloylaminopropylammonium bromide, trimethylmethacryloylaminopropylammonium chloride, trimethylmethacryloylaminopropylammonium bromide, dimethyldiallylammonium chloride and dimethyldiallylammonium bromide; phosphine compounds such as triphenylphosphine; phosphonium salts such as ethyltriphenylphosphonium chloride, ethyltriphenylphosphonium bromide, tetraphenylphosphonium chloride, tetraphenylphosphonium bromide, benzyltriphenylphosphonium chloride and benzyltriphenylphosphonium bromide; hydroxides such as sodium hydroxide, potassium hydroxide and lithium hydroxide; and carbonates such as potassium carbonate and calcium carbonate.

Among these, in view of easy availability and addition reaction rate, tin chloride, pyridine, isoquinoline, quinoline, 2,4,6-tris(dimethylaminomethyl)-phenol, triethylamine, triphenylphosphine, benzyltrimethylammonium salts such as benzyltrimethylammonium chloride and benzyltrimethylammonium bromide, benzyltriethylammonium salts such as benzyltriethylammonium chloride and benzyltriethylammonium bromide, ethyltriphenylphosphonium salts such as ethyltriphenylphosphonium chloride and ethyltriphenylphosphonium bromide, tetraphenylphosphonium salts such as tetraphenylphosphonium chloride and tetraphenylphosphonium bromide, and benzyltriphenylphosphonium salts such as benzyltriphenylphosphonium chloride and benzyltriphenylphosphonium bromide are particularly preferred.

In view of prevention of the catalyst from oozing out after the curing of the polymerzable compound of the present invention, it is preferred to use a catalyst having a radical polymerization-functional group. Specific examples of the catalyst having a radical polymerization-functional group may include 2-vinylpyridine, 3-vinylpyridine, 4-vinylpyridine, N,N-dimethylaminoethyl methacrylate, N,N-dimethylaminoethyl acrylate, N-(3-N',N'-dimethylaminopropyl)-acrylamide, N-(3-N',N'-dimethylaminopropyl)-methacrylamide, trimethylmethacryloyloxyethylammonium salts such as trimethylmethacryloyloxyethylammonium chloride and trimethylmethacryloyloxyethylammonium bromide, trimethylacryloyloxyethylammonium salts such as trimethylacryloyloxyethylammonium chloride and trimethylacryloyloxyethylammonium bromide, trimethylacryloy laminopropylammonium salt such as trimethylacryloylaminopropylammonium chloride and trimethylacryloylaminopropylammonium bromide, trimethylmethacryloylaminopropylammonium salts such as trimethylmethacryloylaminopropylammonium chloride and trimethylmethacryloylaminopropylammonium bromide, dimethyldiallylammonium salts such as dimethyldiallylammonium chloride and dimethyldiallylammonium bromide, and vinylpyridinium salts such as 2-vinylpyridinium chloride, 2-vinylpyridinium bromide, 3-vinylpyridinium chloride, 3-vinylpyridinium bromide, 4-vinylpyridinium chloride and 4-vinylpyridinium bromide. However, the catalyst is of course not limited to these specific examples.

In view of inhibition of oozing out of the catalyst after the curing of the polymerzable compound of the present invention, easy availability and addition reaction rate, 2-vinylpyridine, 3-vinylpyridine, 4-vinylpyridine, N,N-dimethylaminoethyl methacrylate, N,N-dimethylaminoethyl acrylate, N-(3-N',N'-dimethylaminopropyl)-acrylamide, N-(3-N',N'-dimethylaminopropyl)-methacrylamide, trimethylmethacryloyloxyethylammonium salts such as trimethylmethacryloyloxyethylammonium chloride and trimethylmethacryloyloxyethylammonium bromide, trimethylacryloyloxyethylammonium salts such as trimethylacryloyloxyethylammonium chloride and trimethylacryloyloxyethylammonium bromide, trimethylacryloylaminopropylammonium salts such as trimethylacryloylaminopropylammonium chloride and trimethylacryloylaminopropylammonium bromide, trimethylmethacryloylaminopropylammonium salts such as trimethylmethacryloylaminopropylammonium chloride and trimethylmethacryloylaminopropylammonium bromide, and dimethyldiallylammonium salts such as dimethyldiallylammonium chloride and dimethyldiallylammonium bromide are particularly preferred.

In formula (4), $R^4$ represents an organic residue derived from an alcohol compound, a phenol compound or a carboxylic acid compound.

Examples of the "alcohol compound", "phenol compound" and "carboxylic acid compound" may include those mentioned herein-above with respect to $R^2$ in formulae (1), including those mentioned as being preferred.

Particularly, in view of easy availability, the organic residue contained in $R^4$ of formula (4) is preferably an organic residue derived from ethylene glycol, propylene glycol, 1,3-propanediol, 1,4-butanediol, 1,6-hexanediol, neopentyl glycol, glycerin, trimethylolethane, trimethylolpropane, 1,4-cyclohexanediol, 1,4-cyclohexanedimethanol, bisphenol A, bisphenol A propylene oxide adduct, bisphenol A ethylene oxide adduct, brominated bisphenol A, hydrogenated bisphenol A, bisphenol F, phenol novolak resin, cresol novolak resin, 1,2-cyclohexane-dicarboxylic acid, 1,3-cyclohexanedicarboxylic acid, 1,4-cyclohexanedicarboxylic acid, 3-cyclohexene-1,2-dicarboxylic acid, phthalic acid, isophthalic acid and terephthalic acid.

The compound represented by formula (4) includes an epoxy resin. The epoxy resin is described in detail in *Dictionary of Engineering Plastics,* supra. The epoxy resin is of course not limited thereto. As mentioned above, where an epoxy resin is used as the compound of formula (4), the polymerizable compound of the present invention may be referred to as "modified epoxy resin" in view of the starting material.

In the compound represented by formula (4), q is not particularly limited insofar as it is an integer of 1 or more. q is preferably an integer of 2 to 20.

In formula (5), each $R^5$ independently represents at least one organic residue selected from an alkylene group, a branched alkylene group, a cycloalkylene group and an arylene group.

Specific examples of $R^5$ in formula (5) may include those groups mentioned herein-above with respect to $R^1$ in formulae (1) and (2), including those mentioned as being preferred.

In formula (5), the term "each $R^4$ independently represents" means that $R^4$s in the number of n may be different from each other. In other words, it is possible that $R^4$s in the number of n have the same structure, a part of $R^4$s in the number of n have the same structure with the remaining having different structures, or $R^4$s in the number of n have n kinds of structures.

In the present invention (II), the combination of $R^4$ of formula (4) and $R^5$ of formula (5) is preferably such that $R^4$ in formula (4) is at least one organic residue derived from at least one compound selected from ethylene glycol, diethylene glycol, triethylene glycol, tetraethylene glycol, propylene glycol, dipropylene glycol, tripropylene glycol, tetraethylene glycol, 1,4-butanediol, 1,6-hexanediol, 1,8-octanediol, neopentyl glycol, 1,2-cyclohexanediol, 1,3- cyclohexanediol, 1,4-cyclohexanediol, 1,4-cyclohexanedimethanol, hydrogenated bisphenol A, tricyclo[5.2.1.0$^{2.6}$]decanedimethanol, bisphenol A ethylene oxide adduct, bisphenol A propylene oxide adduct, glycerin, trimethylolpropane, trimethylolethane, pentaerythritol, diglycerin, phenol, catechol, bisphenol A, brominated bisphenol A, bisphenol F, phenol novolak resin, cresol novolak resin, benzoic acid, maleic acid, maleic anhydride, fumaric acid, 1,2-cyclohexanedicarboxylic acid, 1,2-cyclohexanedicarboxylic anhydride, 1,3-cyclo-hexanedicarboxylic acid, 1,4-cyclohexanedicarboxylic acid, 3-cyclohexene-1,2-dicarboxylic acid, 4-methyl-4-cyclo-hexene-1,2-dicarboxylic acid, phthalic acid, phthalic anhydride, isophthalic acid and terephthalic acid, and R$^5$ in formula (5) is at least one organic residue selected from a methylene group, an ethylene group, a propylene group, a butylene group, a hexylene group, an octylene group, a cyclopentylene group, a cyclohexylene group, a dicyclopentylene group, a methylethylene group, a phenylethylene group, a 1,2-diphenylethylene group, a phenylene group and a naphthylene group.

Among these, in view of easy availability of raw materials and ease of synthesis, preferred is a combination where R$^4$ in formula (4) is at least one organic residue derived from at least one compound selected from ethylene glycol, propylene glycol, 1,3-propanediol, 1,4-butanediol, 1,6-hexanediol, neopentyl glycol, glycerin, trimethylolethane, trimethylolpropane, 1,4-cyclohexanediol, 1,4-cyclohexanedimethanol, bisphenol A, bisphenol A propylene oxide adduct, bisphenol A ethylene oxide adduct, brominated bisphenol A, hydrogenated bisphenol A, bisphenol F, phenol novolak resin, cresol novolak resin, 1,2-cyclohexanedicarboxylic acid, 1,3-cyclohexanedicarboxylic acid, 1,4-cyclohexanedicarboxylic acid, 3-cyclohexene-1,2-dicarboxylic acid, phthalic acid, isophthalic acid and terephthalic acid, and R$_5$ in formula (5) is at least one organic residue selected from those represented by formulae (6) to (12).

In the process of the present invention (II), it is preferred for the purpose of increasing the curing rate of the polymerizable compound of the present invention (I) to use a compound represented by the following formula (13) in combination with the at least one carboxylic acid represented by formula (5):

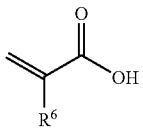

(13)

wherein R$^6$ represents H or CH$_3$.

That is, the compound of formula (13) is acrylic acid where R$^6$ is H, and the compound of formula (13) is methacrylic acid where R$^6$ is CH$_3$.

In the process of the present invention (II), when the compound represented by formula (13) is used, only acrylic acid, only methacrylic acid or both of acrylic acid and methacrylic acid may be used as the compound of formula (13).

Further, a carboxylic acid other than the compound of formula (13) may be used in combination with the at least one carboxylic acid represented by formula (5), insofar as the curability of the polymerizable of the present invention (I) is not deteriorated. The carboxylic acid other than the compound of formula (13) usable in combination with the at least one carboxylic acid represented by formula (5) may include acetic acid, propionic acid, butylic acid, benzoic acid, 1-phenylbenzoic acid, 2-phenylbenzoic acid, 4-phenylbenzoic acid and diphenylacetic acid. However, the usable acidic acid is of course not limited to these acids.

In the addition reaction in the process of the present invention (II), the reaction temperature is not particularly limited but is generally from 0 to 200° C., preferably from 20 to 150° C., more preferably from 50 to 120° C. If the reaction temperature is less than 0° C., the reaction may proceed very slowly, whereas if it exceeds 200° C., polymerization or decomposition may be disadvantageously caused.

In the addition reaction, a solvent may be used. Particularly, in the case where the raw material used is solid or has a high viscosity, stirring is difficult and therefore, a solvent is preferably used. The solvent which can be used is not particularly limited insofar as it does not inhibit the addition reaction, however, examples thereof include toluene, xylene, methyl ethyl ketone, methyl acetate, ethyl acetate, propyl acetate and butyl acetate. These solvents may be used individually or in combination of two or more thereof. Among these, toluene and xylene are preferred.

As for the ratio of raw materials charged for the addition reaction, the total amount of the compounds represented by formulae (5) and (13) may be from 0.5 to 1.5 mol, preferably from 0.8 to 1.2 mol, more preferably from 0.9 to 1.1 mol, per 1 mol of the epoxy group in the compound represented by formula (4). If the total amount of the compound represented by formulae (5) and (13) is less than 0.5 mol per 1 mol of the epoxy group in the compound represented by formula (4), the amount of objective polymerizable compound may decrease to fail in attaining satisfactory curing, whereas if it exceeds 1.5 mol, the compound represented by formula (5) becomes excessive and insufficient curing may disadvantageously result.

The ratio of the charged raw materials of the compound of formula (5) to the compound of formula (13) is not particularly limited but is preferably in a range of 0 to 10, more preferably in a range of 0 to 5.

The amount of the catalyst used in the process of the present invention (II) may generally be from 0.01 to 10 mass %, preferably from 0.1 to 5 mass %, based on the total mass of the compounds represented by formulae (4), (5) and (13). If the amount of catalyst is less than 0.01 mass %, the heating time may become long due to a low reaction rate and the modified epoxy resin produced may undergo thermal polymerization, whereas if the amount of catalyst exceeds 10 mass %, this may cause coloration or is not preferred in view of profitability.

In the process, a polymerization inhibitor can be used so as to inhibit the thermal polymerization of the modified epoxy resin produced. The polymerization inhibitor used is not particularly limited but examples thereof may include p-benzoquinone, 2,5-diphenyl-p-benzoquinone, hydroquinone, hydroquinone monomethyl ether, p-t-butylcatechol, 2,5-di-t-butylhydroquinone, mono-t-butylhydroquinone, and phenolic compounds represented by the following formulae (14) to (23).

(14)
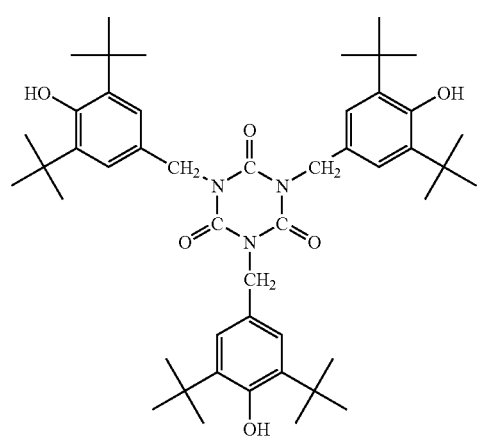
(15)
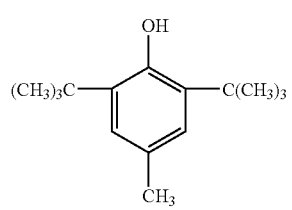
(16)
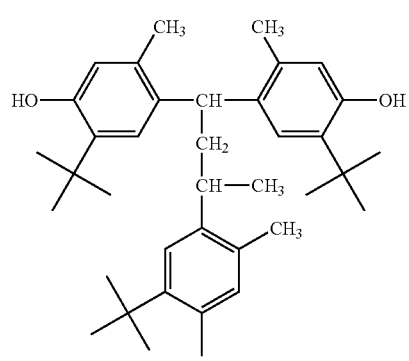
(17)
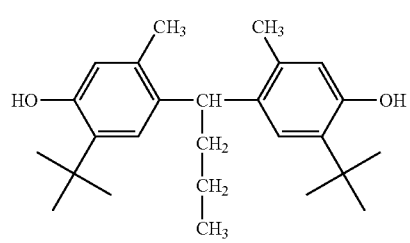
(18)
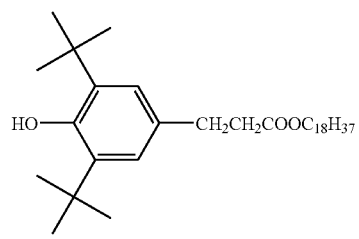
(19)
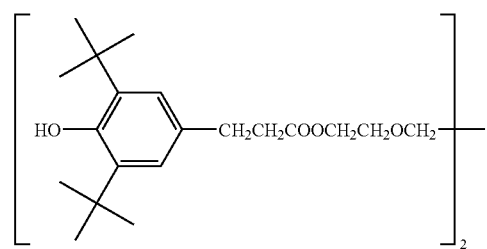
(20)
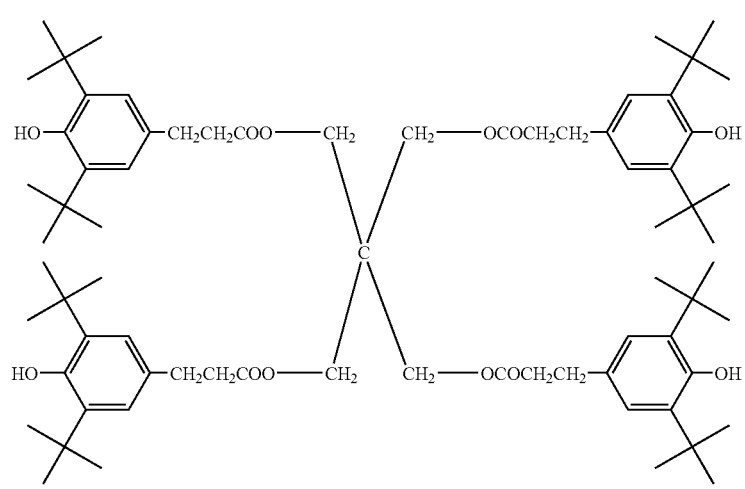

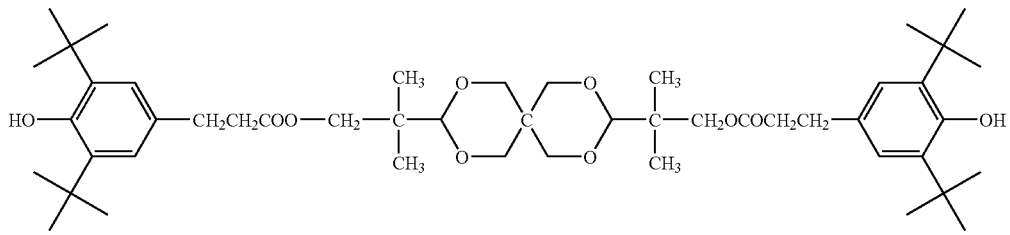
(21)

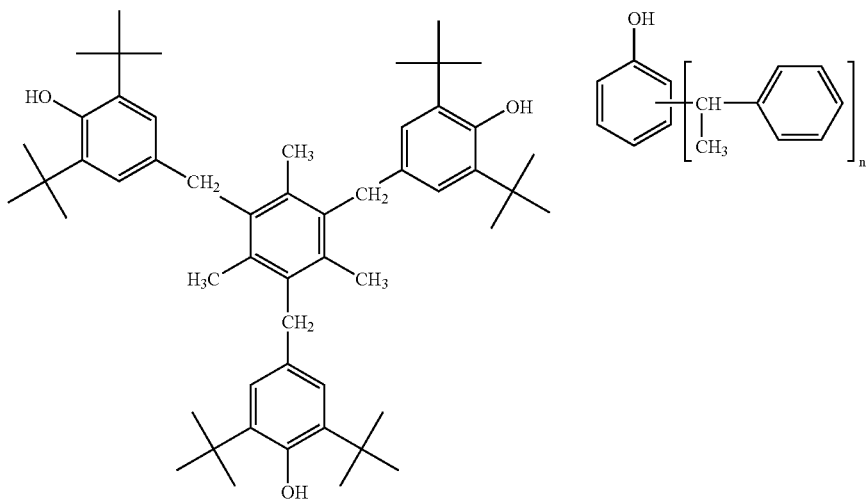
(22) (23)

The present invention (III) is described in detail below.

The present invention (III) relates to a polymerizable composition comprising at least one polymerizable compound of the present invention (I) as an essential component.

The polymerizable composition of the present 23 invention (III) can be obtained by mixing, if desired, (2) various polymerizable monomers, solvents, photopolymerization sensitizers and the like with the polymerizable compound of the present invention (I).

The polymerizable composition of the present invention (III) may contain a polymerizable monomer. The polymerizable monomer which can be used is not particularly limited insofar as it has polymerizability, however, examples thereof may include acrylic acid, methyl acrylate, ethyl acrylate, methacrylic acid, methyl methacrylate, ethyl methacrylate, styrene, monoallyl maleate, monoallyl fumarate, diallyl maleate, diallyl fumarate, mono(allyloxyethyl)maleate, mono(allyloxyethyl)fumarate, bis(allyloxyethyl)maleate and bis(allyloxyethyl)fumarate. These polymerizable monomers may be used individually or in combination of two or more thereof.

The polymerizable composition of the present invention (III) may contain a solvent so as to control the viscosity. The solvent which can be used is not particularly limited insofar as it is a solvent generally used, however, examples thereof may include methyl acetate, ethyl acetate, propyl acetate, butyl acetate, methyl ethyl ketone, toluene and xylene. These solvents can be used individually or in combination of two or more thereof.

Also, the polymerizable composition of the present invention (III) may contain a photopolymerization sensitizer. The photopolymerization sensitizer which can be used is not particularly limited insofar as it is a photopolymerization sensitizer generally used, however, examples thereof may include thiopyrylium salt, merocyanine, quinoline, stilquinoline, aryl ketones, aromatic ketones and ketocoumarins.

The polymerizable composition of the present invention (III) can be cured by heat, an electron beam or γ rays without using a catalyst. Particularly, in the case of heat curing, a thermal polymerization initiator is preferably used so as to reduce the curing temperature or increase the curing rate.

The present invention (IV) is described in detail below.

The present invention (IV) relates to the polymerizable composition of the present invention (III), which contains from 0.1 to 10 parts by mass of at least one radical polymerization initiator per 100 parts by mass of all curable components in the polymerizable composition.

The radical polymerization initiator for use in the present invention (IV) is not particularly limited insofar as it is a radical polymerization initiator generally used.

In the case of a thermal polymerization initiator, examples thereof may include azo-type initiators such as 2,2'-azobisisobutyronitrile and 2,2'-azobisisovaleronitrile; ketone peroxides such as methyl ethyl ketone peroxide, methyl isobutyl ketone peroxide and cyclohexanone peroxide; diacyl peroxides such as benzoyl peroxide, lauroyl peroxide and decanoyl peroxide; peroxyketals such as 1,1-di-t-butylperoxycyclohexane and 2,2-di-(t-butylperoxy)butane; alkyl peroxyesters such as t-butyl peroxypivalate, t-butyl peroxy-2-ethylhexanoate, t-butyl peroxyisobutylate, di-t-butyl peroxyhexahydroterephthalate, di-t-butyl peroxyazelate, t-butyl peroxy-3,5,5-trimethylhexanoate, t-butyl peroxyacetate, t-butyl peroxybenzoate and di-t-butyl peroxytrimethyladipate; and peroxycarbonates such as diisopropyl peroxydicarbonate, di-sec-butyl peroxydicarbonate and t-butyl peroxyisopropylcarbonate. These thermal polymerization initiators can be used individually or in combination of two or more thereof.

When a redox polymerization initiator is used, the polymerization can be performed in the vicinity of ordinary temperature. Examples of the redox polymerization initiator which can be used include a combination of a ketone peroxide and an organic acid salt of metal, such as a combination of methyl ethyl ketone peroxide and cobalt naphthenate, a combination of cumene peroxide and manganese naphthenate, a combination of benzoyl peroxide and cobalt naphthenate, a combination of acetoacetic acid ester peroxide and cobalt naphthenate; and a combination of a peroxide and an aromatic tertiary amine, such as a combination of benzoyl peroxide and N,N-dimethylaniline, a combination of t-butyl hydroperoxide and N,N-dimethyl-p-toluidine, and a combination of dibenzoyl peroxide and N,N-dimethylaniline.

Examples of the active energy ray may include near infrared rays, visible rays, ultraviolet rays, vacuum infrared rays, Xrays, γ rays and an electron beam.

Specific examples of the radical polymerization initiator for use in the polymerization by the irradiation of visible ray or ultraviolet ray may include acetophenone and derivatives thereof, such as acetophenone, 2,2-dimethoxy-2-phenylacetophenone, diethoxyacetophenone, 1-hydroxycyclo-hexyl phenyl ketone, 2-methyl-1-[4-(methylthio)phenyl]-2-morpholinopropan-1-one, 1,2-benzyl-2-methylamino-1-(4-morpholinophenol)butanone, 1,2-hydroxy-2-methyl-1-phenylpropan-1-one; benzophenone and derivatives thereof, such as benzophenone, 4,4'-bis(dimethylamino)benzophenone, 4-trimethylsilylbenzophenone and 4-benzoyl-4'-methyldiphenylsulfide; benzoin and derivatives thereof, such as benzoin, benzoin ethyl ether, benzoin propyl ether, benzoin isobutyl ether and benzoin isopropyl ether; methyl phenyl glyoxylate, benzoin dimethyl ketal, 2,4,6-trimethylbenzoyl-diphenylphosphine oxide, bis(2,6-dichlorobenzoyl)-phenylphosphine oxide, bis(2,6-dichlorobenzoyl)-2,5-dimethylphenylphosphine oxide, bis(2,6-dichlorobenzoyl)-4-ethoxyphenylphosphine oxide, bis(2,6-dichlorobenzoyl)-4-biphenylphosphine oxide, bis(2,6-dichlorobenzoyl)-4-propylphenylphosphine oxide, bis(2,6-dichlorobenzoyl)-2-naphthylphosphine oxide, bis(2,6-dichlorobenzoyl)-1-naphthylphosphine oxide, bis(2,6-dichlorobenzoyl-4-chlorophenylphosphine oxide, bis(2,6-dichlorobenzoyl)-2,4-dimethoxyphenylphosphine oxide, bis(2,6-dichlorobenzoyl)-decylphosphine oxide, bis(2,6-dichlorobenzoyl)-4-octylphenylphosphine oxide, bis(2,6-dichlorobenzoyl)-2,5-dimethylphenylphosphine oxide, bis(2,6-dichlorobenzoyl)-phenylphosphine oxide, bis(2,4,6-trimethylbenzoyl)-2,5-dimethylphenylphosphine oxide, bis(2,6-dichloro-3,4,5-trimethoxybenzoyl)-2,5-dimethylphenylphosphine oxide, bis(2,6-dichloro-3,4,5-trimethoxybenzoyl)-4-ethoxyphenylphosphine oxide, bis(2-methyl-1-naphthoyl)-2,5-dimethylphenylphosphine oxide, bis(2-methyl-1-naphthoyl)-2,5-phenylphosphine oxide, bis(2-methyl-1-naphthoyl)-4-biphenylylphosphine oxide, bis(2-methyl-1-naphthoyl)-4-ethoxybiphenylphosphine oxide, bis(2-methyl-1-naphthoyl)-2-naphthylphosphine oxide, bis(2-methyl-1-naphthoyl)-4-propylphenylphosphine oxide, bis(2-methoxyl-1-naphthoyl)-2,5-dimethylphenylphosphine oxide, bis(2-methoxyl-1-naphthoyl)-4-methoxyphenylphosphine oxide, bis(2-methoxyl-1-naphthoyl)-4-biphenylylphosphoine oxide, bis(2-chloro-1-naphthoyl)-2,5-dimethylphenylphosphine oxide and bis(2,6-dimethoxybenzoyl)-2,4,6-trimethylpentylphosphine oxide.

Specific examples of the polymerization initiator sensitive to visible ray may include bis($\eta^5$-2,4-cyclopentadiene-1-yl)-bis(2,6-difluoro-3-(1H-pyrrole-1-yl)-phenyl)-titanium (trade name of IIRGACURE 784, Ciba Specialty Chemicals K.K.).

Specific examples of the polymerization initiator sensitive to visible rays and/or near infrared rays may include a combination of a visible light- and/or near infrared light-absorbing cationic dye represented by the following formula (24), having light sensitivity in the visible light or near infrared light region, and a boron compound represented by the following formula (25).

$$D^+ \cdot A^- \quad (24)$$

wherein $D^+$ represents a cationic dye having absorption in the near infrared light region, and $A^-$ represents various anion;

(25)

wherein $Z^+$ represents an arbitrary cation, and $R^7$ to $R^{10}$ each independently represents an alkyl group, an aryl group, an allyl group, an aralkyl group, an alkenyl group, an alkynyl group, a silyl group, a heterocyclic group, a halogen atom, a substituted alkyl group, a substituted aryl group, a substituted allyl group, a substituted aralkyl group, a substituted alkenyl group, a substituted alkynyl group or a substituted silyl group.

The cationic dye represented by formula (24) is specifically a dye having absorption in an arbitrary wavelength region usually in the range from 400 to 2,000 nm, preferably from 500 to 1,500 nm.

Preferred examples of the cation ($D^+$) for use in the present invention may include cations of methine-, polymethine-, indoline-, cyanine-, xanthene-, oxazine-, thiazine-, diaryl methane-, triaryl methane- and pyrylium-series cationic dyes. Representative examples of the cationic dye may include cations represented by the following structural formulae (26) to (39).

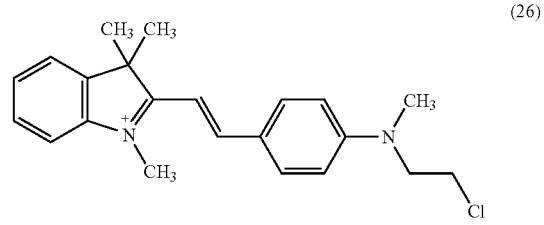

(26)

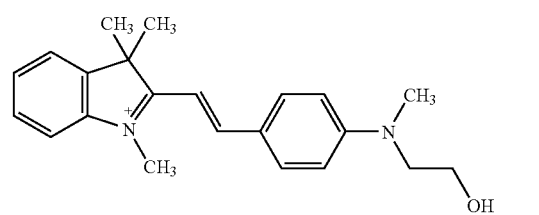

(27)

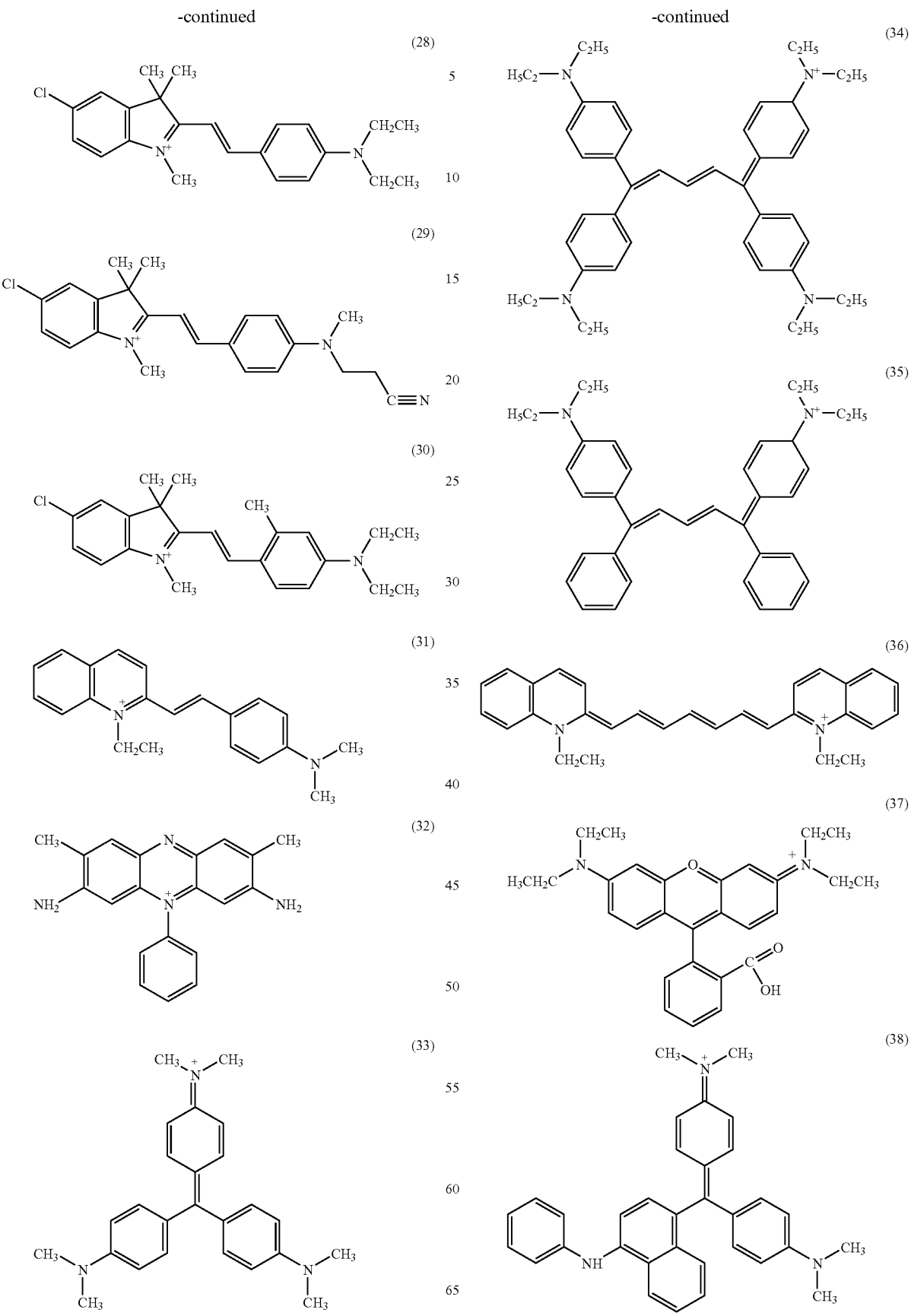

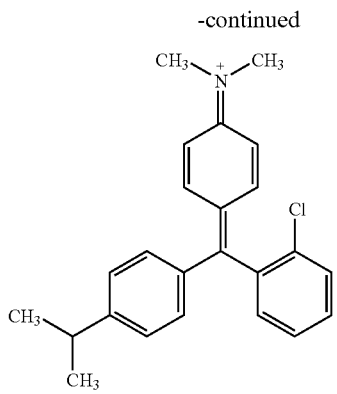
(39)

The counter anion A⁻ is an arbitrary anion but is preferably a 4-coordinate borate anion represented by the following formula (40):

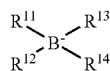
(40)

wherein $R^{11}$ to $R^{14}$ each independently represents an alkyl group, an aryl group, an allyl group, an aralkyl group, an alkenyl group, an alkynyl group, a silyl group, a heterocyclic group, a halogen atom, a substituted alkyl group, a substituted aryl group, a substituted allyl group, a substituted aralkyl group, a substituted alkenyl group, a substituted alkynyl group or a substituted silyl group.

Specific examples thereof may include an n-butyltriphenyl borate ion, an n-octyltriphenyl borate ion, a triphenylsilyltriphenyl borate ion, a di-n-dodecyldiphenyl borate ion, a tetraphenyl borate ion and a tri-n-butyl(dimethylphenylsilyl)borate ion. More specific examples thereof include anions described in Japanese unexamined Patent Publication No. 6-75374 (JP-A-6-75374).

In the boron-containing catalyst represented by formula (25), specific examples of the 4-coordinate borate ion as an anion may include an n-butyltriphenyl borate ion, an n-octyltriphenyl borate ion, a triphenylsilyltriphenyl borate ion, an n-butyltrianisyl borate ion, an n-butyltri(p-fluorophenyl)borate ion, an n-butyltri(p-trifluoromethylphenyl)borate ion, a di-n-dodecyldiphenyl borate ion, a tetraphenyl borate ion, a triphenylnaphthyl borate ion, a tetrabutyl borate ion and a tri-n-butyl(dimethylphenylsilyl)borate ion.

Examples of the cation ($Z^+$) in the formula may include a quaternary ammonium cation represented by the following formula (41), a quaternary pyridinium cation, a quaternary quinolinium cation, a diazonium cation, a tetrazolium cation, a phosphonium cation, an (oxo)sulfonium cation, metal cations such as sodium, potassium, lithium, magnesium and calcium, organic acid cations such as flavylium salt and pyranium salt, carbocations such as tropylium and cyclopropylium, halogenium cations such as iodonium, and cations of metal compounds such as arsenic, cobalt, chromium, palladium, titanium, tin and antimony. These are described in more detail in JP-A-6-75374. These cationic dyes and boron-containing catalysts can be used individually or in combination of two or more thereof.

(41)

wherein $R^{15}$ to $R^{18}$ each independently represents a hydrogen atom, an alkyl group, an aryl group, an allyl group, an aralkyl group, an alkenyl group, an alkynyl group, a heterocyclic group, a substituted alkyl group, a substituted aryl group, a substituted allyl group, a substituted aralkyl group, a substituted alkenyl group or a substituted alkynyl group.

These radical polymerization initiators for use in the polymerization by near-infrared rays, visible rays or ultraviolet rays can be used individually or in combination of two or more thereof.

Also, a thermal polymerization initiator, a redox polymerization initiator and a radical polymerization initiator sensitive to ultraviolet rays, visible rays or near-infrared rays may be used as a mixture.

The radical polymerization initiator may preferably be incorporated in an amount of 0.1 to 10 parts by mass, more preferably 0.3 to 7 parts by mass, particularly preferably 0.5 to 5 parts by mass, per 100 parts by mass of the all curable components in the polymerizable composition. If the amount is less than 0.1 part by mass, the curing of the composition may be insufficient. The addition in an amount of more than 10 parts by mass is economically inadvantageous.

The present invention (V) relates to a cured product obtained by curing the polymerizable composition of the present invention (III) or (IV), and a production process of the cured product.

Namely, the cured product of the present invention (V) can be obtained by the radical polymerization or the like of the polymerizable composition of the present invention (III) or (IV).

The curing in the present invention (V) includes heat curing and/or curing by an active energy ray. In particular, heat curing and/or curing by near infrared rays, visible rays, ultraviolet rays or an electron beam are preferred, and heat curing and/or curing by visible rays or ultraviolet rays are more preferred. The cured product may also be obtained by using two or more different curing methods in combination.

In heat-curing a composition not containing a radical polymerization initiator, the reaction temperature may usually be from 50 to 300° C., preferably from 100 to 250° C. If the reaction temperature is less than 50° C., the curing may hardly proceed, whereas if it exceeds 300° C., the polymerization composition and the cured product may decompose.

In the curing by a thermal polymerization initiator or a redox polymerization initiator, the optimal temperature for curing is governed by the temperature where a radical is generated.

Of active energy rays, examples of the light source which can be used for curing by visible rays or ultraviolet rays may include a low-pressure mercury lamp, a high-pressure mercury lamp, an extra-high pressure mercury lamp, a deuterium lamp, a metal halide lamp, a halogen lamp, a xenon lamp, a tungsten lamp, a gallium lamp, a carbon arc lamp, an incandescent lamp, a fluorescent lamp, an excimer lamp and laser. Among these light sources, the high-pressure mercury lamp and the metal halide lamp are preferred.

The wavelength of the light source for curing by visible rays or ultraviolet rays may usually be from 200 to 750 nm, preferably from 200 to 450 m, and the irradiation amount is usually from 10 to 1,000 mJ/cm$^2$, preferably from 100 to 700 mJ/cm$^2$.

In the curing using an electron beam, examples of the irradiation system therefor may include a scanning system, a broad beam system, a curtain beam system and an ion plasma system. The irradiation amount is usually from 0.1 Gy to 200 kGy, preferably from 1 Gy to 100 kGy.

The present invention is further illustrated below by referring to Examples, however, the present invention is not limited thereto.

Various physical properties were measured as follows.

1. Refractive Index ($n_D$)

The refractive index ($n_D$) at room temperature was measured using "Abbe Refractometer 1T" manufactured by Atago K.K.

2. Acid Value

The acid value was measured by the acid value testing method described in JIS K0070.

The conversion, yield and purity in reaction were decided from a previously prepared calibration curve by quantitatively determining each component according to an absolute calibration method using a high-performance liquid chromatograph. The column used was Showdex (registered trademark) F-411A (produced by Showa Denko K.K.), the solvent was aqueous 1 wt % phosphoric acid solution/methanol (7/3), the flow rate was 1.0 ml/min, the detector was SPD-10 AVvp (manufactured by Shimadzu Corporation), and the peak of each component was detected at 210 nm.

PRODUCTION EXAMPLE 1

Synthesis of Monoallyl Fumarate (hereinafter Referred to as "H-DAF")

Into a 2 liter flask, 474.25 g (4.837 mol) of maleic anhydride, 260.69 g (4.833 mol) of allyl alcohol and 500 ml of toluene were charged. Under a nitrogen steam, the reaction solution was heated to 60° C. in an oil bath while stirring with a magnetic stirrer. After 14 hours, the heating was stopped and the flask was cooled. To the obtained reactant, 500 ml of toluene and 1 liter of water were added to cause liquid separation and the toluene layer was concentrated by an evaporator to obtain 279.01 g of the objective monoallyl maleate (hereinafter referred to as "H-DAM"). The yield was 37.0%.

Into a 300 ml flask equipped with a refluxing unit, 100.04 g (0.64 mol) of H-DAM synthesized above, 50.00 g of toluene, 1.01 g (1 mass % based on H-DAM) of concentrated hydrochloric acid and 0.01 g of hydroquinone monomethyl ether were charged. Under a nitrogen stream, the reaction solution was heated to 140° C. in an oil bath while stirring with a magnetic stirrer to reflux the toluene. After 4 hours, the heating was stopped and the flask was cooled. To the obtained reactant, 200 ml of toluene was added, the crystal was filtered, and the crystal was washed twice with 100 ml of toluene. The crystal was dissolved in 150 ml of ethyl acetate and insoluble matters were removed by filtration. The filtrate was concentrated by an evaporator to obtain 38.39 g of the objective H-DAF. The yield was 38.4%.

PRODUCTION EXAMPLE 2

Synthesis of Monoallyloxyethyl Fumarate (hereinafter Referred to as "H-BAF")

Into a 2 liter flask, 500 g (5.10 mol) of maleic anhydride, 573 g (5.61 mol) of ethylene glycol monoallyl ether and 0.05 g of hydroquinone monomethyl ether were charged. Under a nitrogen steam, the reaction solution was heated to 50° C. in an oil bath while stirring with a magnetic stirrer. After 24 hours, the heating was stopped and the flask was cooled. The obtained reactant was analyzed by a high-performance liquid chromatograph, as a result, the conversion of maleic anhydride was 95%.

Into a 2 liter flask equipped with a refluxing unit, 499.54 g of the reaction solution prepared above, 215.07 g of toluene, 4.99 g (1 mass % based on raw material) of concentrated hydrochloric acid and 0.25 g of hydroquinone monomethyl ether were charged. Under a nitrogen stream, the reaction solution was heated to 140° C. in an oil bath while stirring with a magnetic stirrer to reflux the toluene. After 3 hours, the heating was stopped and the flask was cooled. To the obtained reactant, 500 ml of toluene was added and the resulting solution was filtered to remove insoluble matters. To this filtrate, 500 ml of water was added to remove hydrochloric acid and liquid separation was performed by a separation funnel. The toluene layer was concentrated by an evaporator to obtain 428 g of the objective H-BAF. The yield was 90% based on the maleic anhydride.

EXAMPLE 1

Into a 1 liter flask, 4004.4 g (2.0 mol) of H-BAF, 374.0 g of ADECARESIN (registered trademark) EP-4100G (bisphenol A diglycidyl ether, epoxy equivalent: 185, produced by Asahi Denka Kogyo K.K.), 5.73 g of TPP-Zc (benzyltriphenylphosphonium chloride, produced by Hokko Kagaku Kogyo K.K.) and 0.4 g of IRGANOX (registered trademark) 1010 (pentaerythrityl-tetrakis[3-(3,5-di-t-butyl-4-hydroxyphenyl)propionate], produced by Ciba Specialty Chemicals K.K.) were charged. Under a nitrogen stream, the reaction mixture was heated to 100° C. in an oil bath while stirring with a magnetic stirrer. The obtained reaction product was designated as "Sample A". Sample A had a refractive index of 1.544 and an acid value of 1.7.

Figure 2:
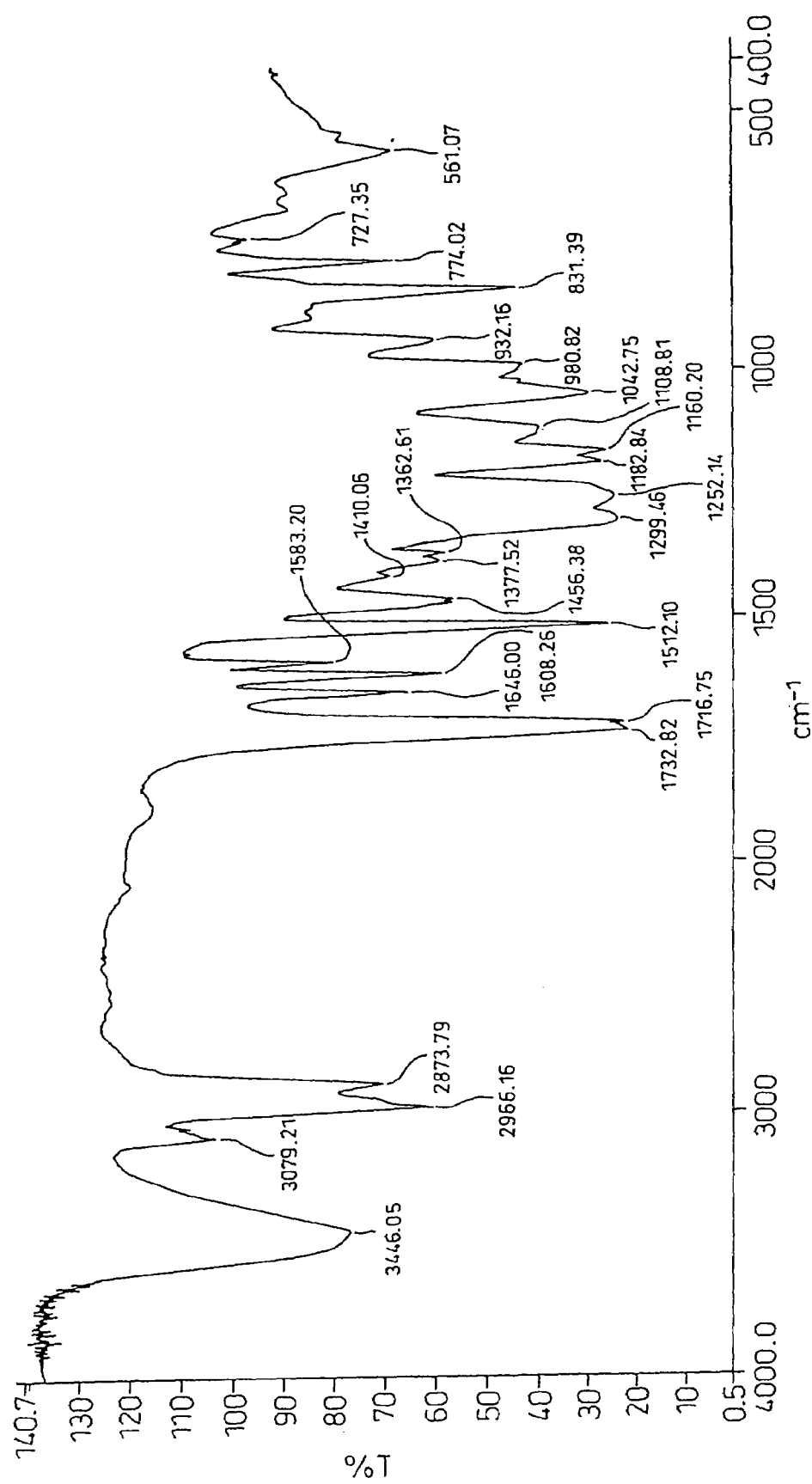
FIG. 2 is an IR spectrum chart of the polymerizable compound obtained in Example 1.

The $^1$H-NMR spectrum chart and IR spectrum chart of Sample A are shown in FIGS. 1 and 2, respectively.

EXAMPLE 2

Into a 1 liter flask, 4004.4 g (2.0 mol) of H-BAF, 307.6 g of ADECAGLYCILOL (registered trademark) ED-505 (trimethylolpropanetriglycidyl ether, epoxy equivalent; 153, produced by Asahi Denka Kogyo K.K.), 4.25 g of TPP-Zc (benzyltriphenylphosphonium chloride, produced by Hokko Kagaku Kogyo K.K.) and 0.42 g of IRGANOX (registered trademark) 1010 (pentaerythrityl-tetrakis[3-(3,5-di-t-butyl-4-hydroxyphenyl)propionate], produced by Ciba Specialty Chemicals K.K.) were charged. Under a nitrogen stream, the reaction mixture was heated to 100° C. in an oil bath while stirring with a magnetic stirrer. The obtained reaction product was designated as "Sample B". Sample B had a refractive index of 1.500 and an acid value of 17.4.

Figure 3:
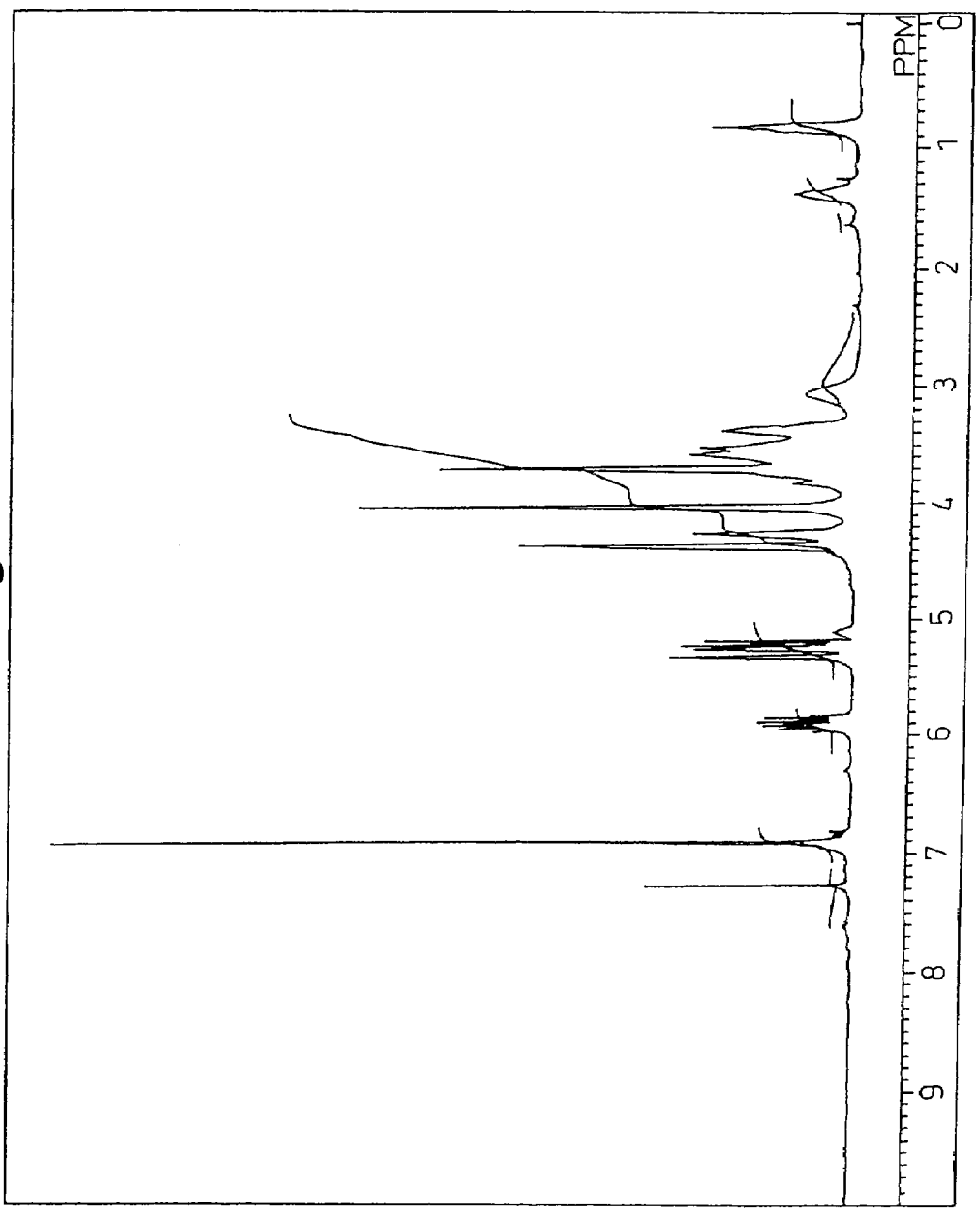
FIG. 3 is a $^1$H-NMR spectrum chart of the polymerizable compound obtained in Example 2.
Figure 4:
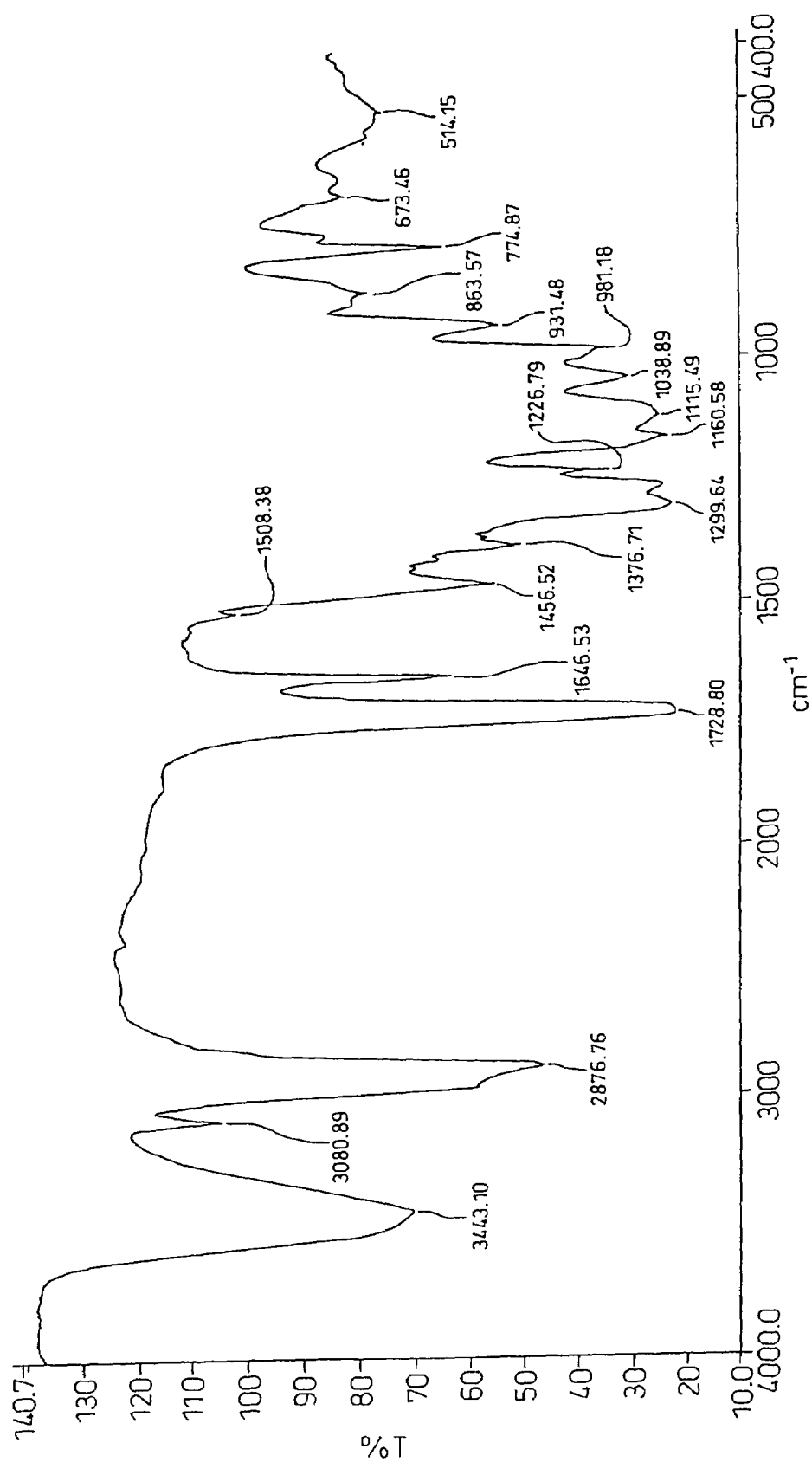
FIG. 4 is an IR spectrum chart of the polymerizable compound obtained in Example 2.

The $^1$H-NMR spectrum chart and IR spectrum chart of Sample B are shown in FIGS. 3 and 4, respectively.

EXAMPLE 3

Into a 1 liter flask, 4004.4 g (2.0 mol) of H-BAF, 446.0 g of ADECARESIN (registered trademark) EP-4080E (hydrogenated bisphenol A diglycidyl ether, epoxy equivalent: 214, produced by Asahi Denka Kogyo K.K.), 6.26 g of TPP-Zc (benzyltriphenylphosphonium chloride, produced by Hokko Kagaku Kogyo K.K.) and 0.4 g of IRGANOX (registered trademark) 1010 (pentaerythrityl-tetrakis[3-(3,5-di-t-butyl-4-hydroxyphenyl)propionate], produced by Ciba Specialty Chemicals K.K.) were charged. Under a nitrogen stream, the reaction mixture was heated to 100° C. in an oil bath while stirring with a magnetic stirrer. The obtained reaction product was designated as "Sample C". Sample C had a refractive index of 1.507 and an acid value of 0.7.

EXAMPLE 4

Into a 1 liter flask, 4004.4 g (2.0 mol) of H-BAF, 446.0 g of ADECARESIN (registered trademark) EP-4088S (trictclo [5.2.1.0$^{2,6}$]decanedimethanol diglycidyl ether, epoxy equivalent: 178, produced by Asahi Denka Kogyo K.K.), 6.26 g of TPP-Zc (benzyltriphenylphosphonium chloride, produced by Hokko Kagaku Kogyo K.K.) and 0.4 g of IRGANOX (registered trademark) 1010 (pentaerythrityl-tetrakis[3-(3,5-di-t-butyl-4-hydroxyphenyl)propionate], produced by Ciba Specialty Chemicals K.K.) were charged. Under a nitrogen stream, the reaction mixture was heated to 100° C. in an oil bath while stirring with a magnetic stirrer. The obtained reaction product was designated as "Sample D". Sample D had a refractive index of 1.511 and an acid value of 12.3.

Figure 5:
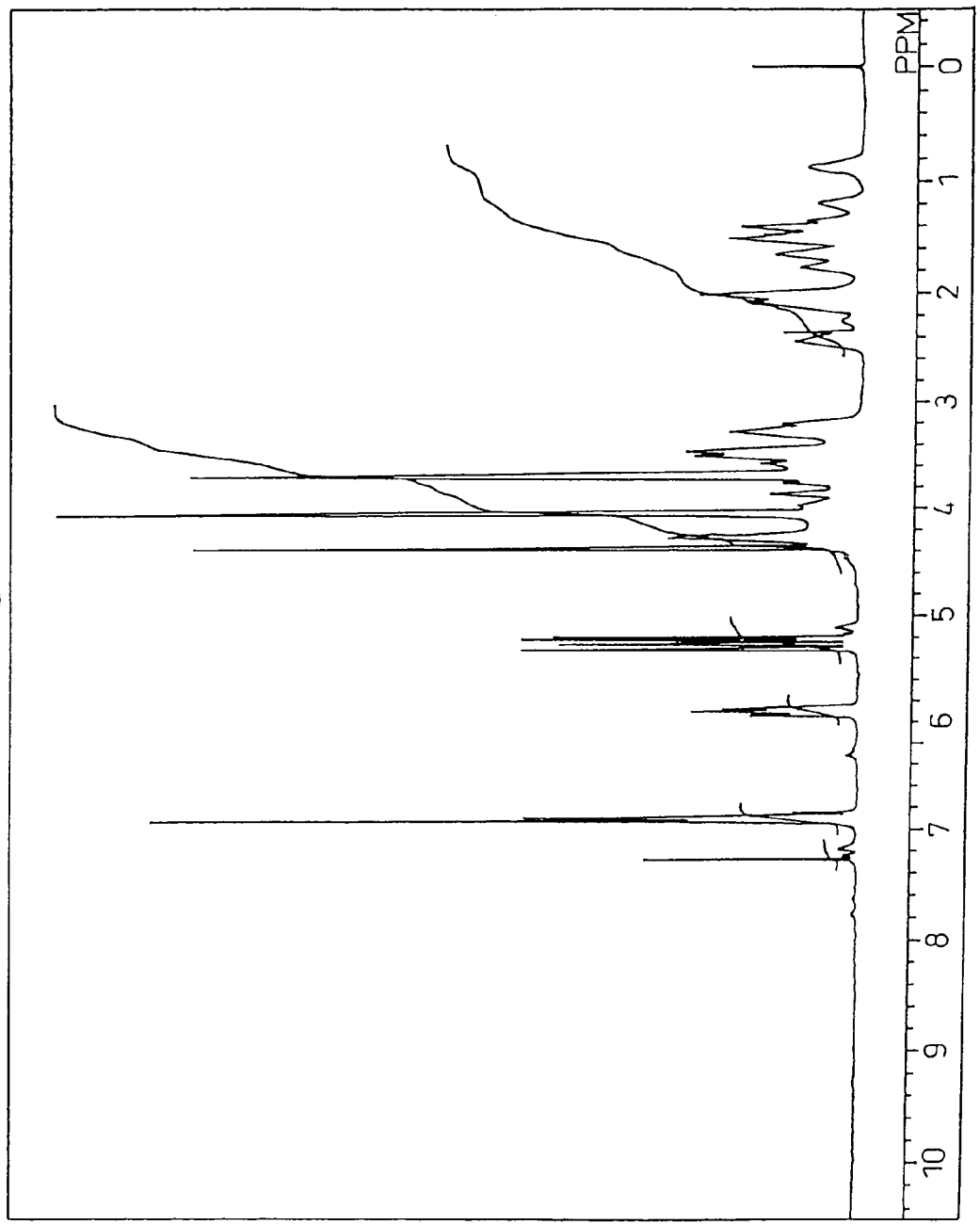
FIG. 5 is a $^1$H-NMR spectrum chart of the polymerizable compound obtained in Example 4.
Figure 6:
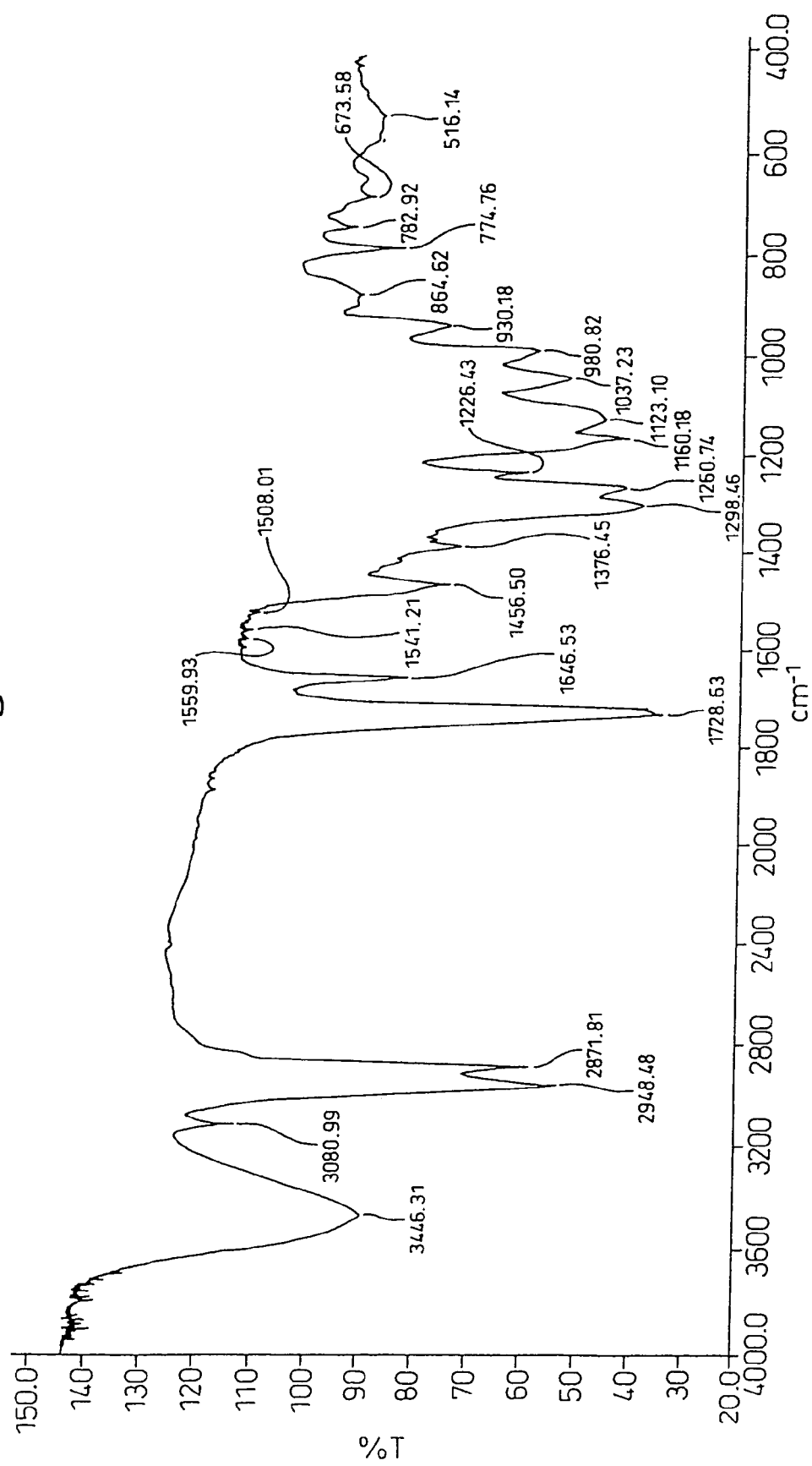
FIG. 6 is an IR spectrum chart of the polymerizable compound obtained in Example 4.

The $^1$H-NMR spectrum chart and IR spectrum chart of Sample D are shown in FIGS. 5 and 6, respectively.

EXAMPLE 5

Into a 1 liter flask, 4004.4 g (2.0 mol) of H-BAF, 292.0 g of ADECARESIN (registered trademark) EP-4085S (1,4-cyclohexanedimethanol diglycidyl ether, epoxy equivalent: 146, produced by Asahi Denka Kogyo K.K.), 5.12 g of TPP-Zc (benzyltriphenylphosphonium chloride, produced by Hokko Kagaku Kogyo K.K.) and 0.4 g of IRGANOX (registered trademark) 1010 (pentaerythrityl-tetrakis[3-(3,5-di-t-butyl-4-hydroxyphenyl)propionate], produced by Ciba Specialty Chemicals K.K.) were charged. Under a nitrogen stream, the reaction mixture was heated to 100° C. in an oil bath while stirring with a magnetic stirrer. The obtained reaction product was designated as "Sample E". Sample E had a refractive index of 1.511 and an acid value of 12.3.

Figure 7:
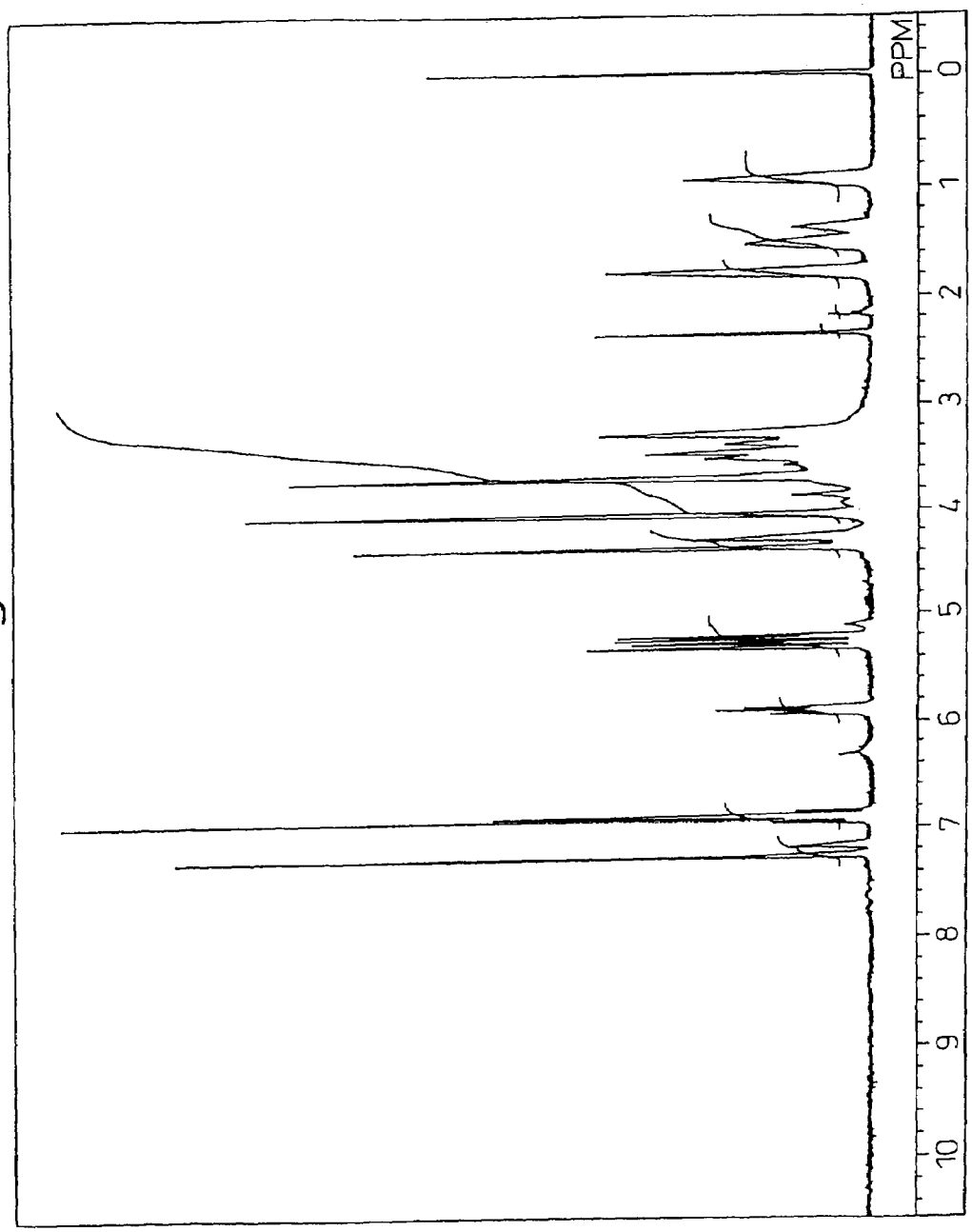
FIG. 7 is a $^1$H-NMR spectrum chart of the polymerizable compound obtained in Example 5.
Figure 8:
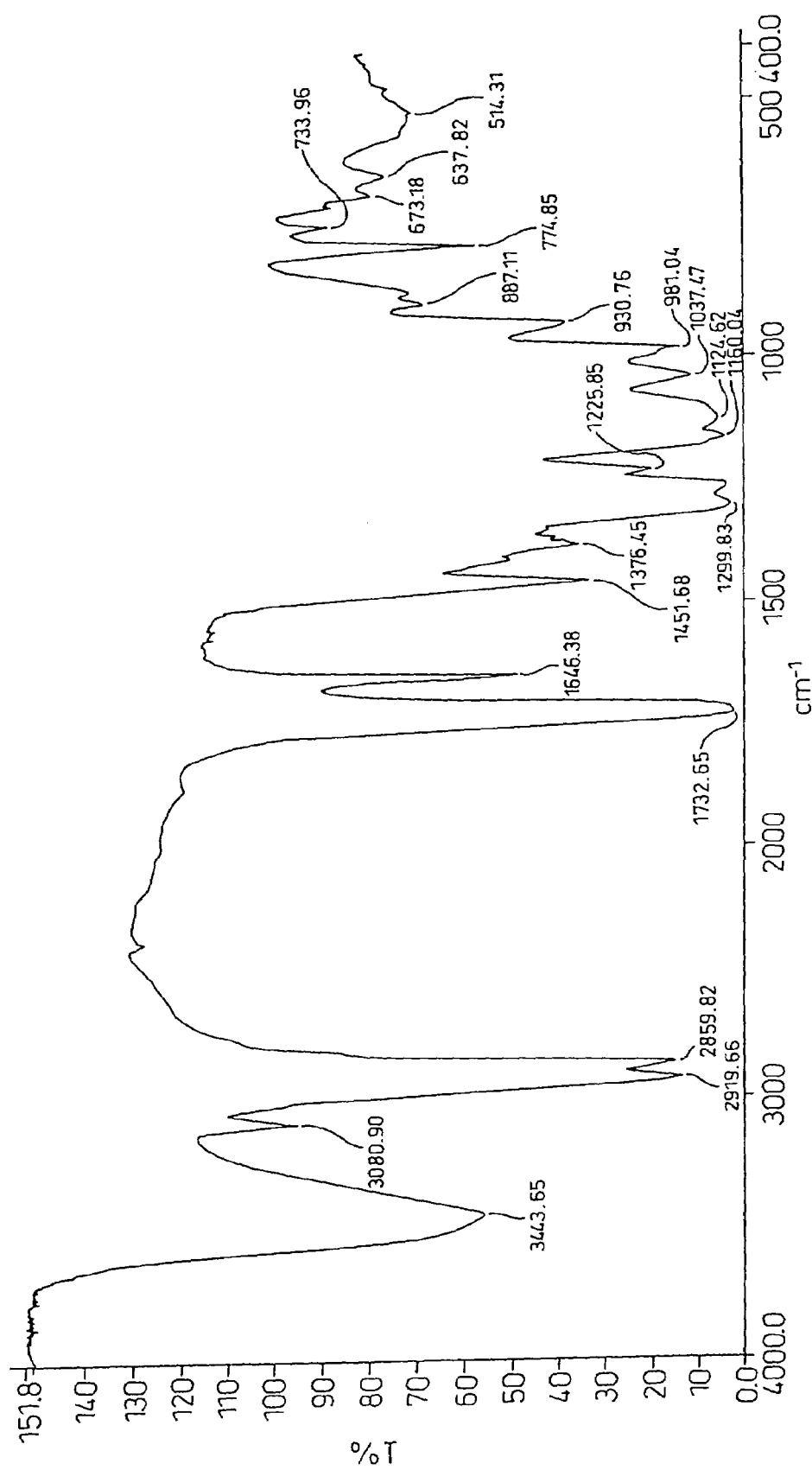
FIG. 8 is an IR spectrum chart of the polymerizable compound obtained in Example 5.

The $^1$H-NMR spectrum chart and IR spectrum chart of Sample E are shown in FIGS. 7 and 8, respectively.

EXAMPLE 6

Into a 300 ml flask, 48.39 g (0.242 mol) of H-BAF, 51.70 g of ARALDITE ECN (registered trademark) 1273 (cresol novolak epoxy resin, epoxy equivalent: 214, produced by Asahi Chiba K.K.), 43.42 g of toluene, 0.50 g of DMP-30 (2,4,6-tris(dimethylaminomethyl)phenol, produced by Wako Pure Chemical Industries, Ltd.) and 0.02 g of hydroquinone monomethyl ether were charged. Under a nitrogen stream, the reaction mixture was heated to 100° C. in an oil bath while stirring with a magnetic stirrer. After 22 hours, the heating was stopped and the flask was cooled. The obtained reaction mixture was analyzed by a high-performance liquid chromatograph, as a result, 0.92 g of the raw material H-BAF was remaining and the conversion of H-BAF was 98.1%. This product was designated as "Sample F".

EXAMPLE 7

Into a 300 ml flask, 12.90 g (0.064 mol) of H-BAF, 4.62 g (0.064 mol) of acrylic acid, 22.91 g of ARALDITE EPN (registered trademark) 1180 (phenol novolak epoxy resin, epoxy equivalent: 179, produced by Asahi Chiba K.K.), 48.24 g of toluene, 0.49 g of DMP-30 (2,4,6-tris(dimethylaminomethyl)phenol, produced by Wako Pure Chemical Industries, Ltd.) and 0.02 g of hydroquinone monomethyl ether were charged. Under a nitrogen stream, the reaction mixture was heated to 100° C. in an oil bath while stirring with a magnetic stirrer. After 13 hours, the heating was stopped and the flask was cooled. The obtained reaction mixture was analyzed by a high-performance liquid chromatograph, as a result, 0.06 g of the raw material H-BAF and 1.21 g of acrylic acid were remaining. The conversion of H-BAF was 99.5% and the conversion of acrylic acid was 76.0%. This product was designated as "Sample G".

EXAMPLE 8

Into a 300 ml flask, 12.90 g (0.064 mol) of H-BAF, 4.63 g (0.064 mol) of acrylic acid, 30.75 g of ARALDITE ECN (registered trademark) 1273 (cresol novolak epoxy resin, epoxy equivalent: 214, produced by Asahi Chiba K.K.), 48.24 g of toluene, 0.49 g of DMP-30 (2,4,6-tris(dimethylaminomethyl)phenol, produced by Wako Pure Chemical Industries, Ltd.) and 0.02 g of hydroquinone monomethyl ether were charged. Under a nitrogen stream, the reaction mixture was heated to 100° C. in an oil bath while stirring with a magnetic stirrer. After 13 hours, the heating was stopped and the flask was cooled. The obtained reaction mixture was analyzed by a high-performance liquid chromatograph, as a result, 0.06 g of the raw material H-BAF and 1.21 g of acrylic acid remained. The conversion of H-BAF was 99.5% and the conversion of acrylic acid was 76.0%. This product was designated as "Sample H".

EXAMPLE 9

Into a 300 ml flask, 58.10 g (0.290 mol) of H-BAF, 42.02 g of ADECAGLYCILOL ED-507 (glycerin triglycidyl ether, epoxy equivalent: 145, produced by Asahi Denka Kogyo K.K.), 0.50 g of DMP-30 (2,4,6-tris(dimethylaminomethyl) phenol, produced by Wako Pure Chemical Industries, Ltd.) and 0.02 g of hydroquinone monomethyl ether were charged. Under a nitrogen stream, the reaction mixture was heated to 100° C. in an oil bath while stirring with a magnetic stirrer. After 20 hours, the heating was stopped and the flask was cooled. The obtained product was designated as "Sample I". Sample I had a refractive index of 1.497 and an acid value of 2.14.

EXAMPLE 10

Into a 300 ml flask, 31.28 g (0.156 mol) of H-BAF, 11.28 g (0.156 mol) of acrylic acid, 57.68 g of ARALDITE AER (registered trademark) 2502 (diglycidyl bisphenol A, epoxy equivalent: 185, produced by Asahi Chiba K.K.), 0.50 g of DMP-30 (2,4,6-tris(dimethylaminomethyl)phenol, produced by Wako Pure Chemical Industries, Ltd.) and 0.02 g of hydroquinone monomethyl ether were charged. Under a nitrogen stream, the reaction mixture was heated to 100° C.

in an oil bath while stirring with a magnetic stirrer. After 11 hours, the heating was stopped and the flask was cooled. The obtained reaction mixture was analyzed by a high-performance liquid chromatograph, as a result, the raw material H-BAF did not remain but 1.21 g of acrylic acid did remain. The conversion of H-BAF was 100% and the conversion of acrylic acid was 89.3%. This product was designated as "Sample J". "Sample A" had a refractive index of 1.546 and an acid value of 1.72.

EXAMPLE 11

Into a 1 liter flask, 400.4 g (2.0 mol) of H-BAF, 374.0 g of ADECARESIN (registered trademark) EP-4100G (bisphenol A diglycidyl ether, epoxy equivalent: 185, produced by Asahi Denka Kogyo K.K.), 8.00 g of N,N-dimethylaminoethyl methacrylate (produced by Kyoeisha Kagaku K.K.) and 0.4 g of IRGANOX (registered trademark) 1010 (pentaerythrityl-tetrakis[3-(3,5-di-t-butyl-4-hydroxyphenyl)propionate], produced by Ciba Specialty Chemicals K.K.) were charged. Under a nitrogen stream, the reaction mixture was heated to 110° C. in an oil bath while stirring with a magnetic stirrer. After 6 hours, the heating was stopped and the flask was cooled. The obtained reaction product was designated as "Sample K". Sample K had a refractive index of 1.544 and an acid value of 6.5.

EXAMPLE 12

Into a 1 liter flask, 400.4 g (2.0 mol) of H-BAF, 374.0 g of ADECARESIN (registered trademark) EP-4100G (bisphenol A diglycidyl ether, epoxy equivalent: 185, produced by Asahi Denka Kogyo K.K.), 8.00 g of trimethyl-methacryloyloxyethylammonium chloride (produced by Kyoeisha Kagaku K.K.) and 0.4 g of IRGANOX (registered trademark) 1010 (pentaerythrityl-tetrakis[3-(3,5-di-t-butyl-4-hydroxyphenyl)propionate], produced by Ciba Specialty Chemicals K.K.) were charged. Under a nitrogen stream, the reaction mixture was heated to 110° C. in an oil bath while stirring with a magnetic stirrer. After 7 hours, the heating was stopped and the flask was cooled. The obtained reaction product was designated as "Sample L". Sample L had a refractive index of 1.544 and an acid value of 6.5.

EXAMPLE 13

Into a 1 liter flask, 400.4 g (2.0 mol) of H-BAF, 374.0 g of ADECARESIN (registered trademark) EP-4100G (bisphenol A diglycidyl ether, epoxy equivalent: 185, produced by Asahi Denka Kogyo K.K.), 0.50 g of CMP-30 (2,4,6,-tris(dimethylaminomethyl)phenol, produced by Wako Pure Chemical Industries, Ltd.) and 0.4 g of IRGANOX (registered trademark) 1010 (pentaerythrityl-tetrakis[3-(3,5-di-t-butyl-4-hydroxyphenyl)propionate], produced by Ciba Specialty Chemicals K.K.) were charged. Under a nitrogen stream, the reaction mixture was heated to 110° C. in an oil bath while stirring with a magnetic stirrer. After 6 hours, the heating was stopped and the flask was cooled. The obtained reaction product was designated as "Sample M". Sample M had a refractive index of 1.544 and an acid value of 1.7.

COMPARATIVE EXAMPLE 1

Into a 200 ml flask, 7.24 g (0.100 mol) of acrylic acid, 18.53 g of ARALDITE AER (registered trademark) 2502 (diglycidyl bisphenol A, epoxy equivalent: 185, produced by Asahi Chiba K.K.), 0.14 g of DMP-30 (2,4,6-tris(dimethylaminomethyl)phenol, produced by Wako Pure Chemical Industries, Ltd.) and 5 mg of hydroquinone monomethyl ether were charged. Under a nitrogen stream, the reaction mixture was heated to 100° C. in an oil bath while stirring with a magnetic stirrer. After 6 hours, the heating was stopped and the flask was cooled. The obtained reaction mixture was analyzed by a high-performance liquid chromatograph, as a result, 0.15 g of the raw material acrylic acid remained and the conversion of acrylic acid was 98.0%. This reaction product was designated as "Sample P".

COMPARATIVE EXAMPLE 2

Into a 200 ml flask, 8.60 g (0.100 mol) of methacrylic acid, 18.54 g of ARALDITE AER (registered trademark) 2502 (diglycidyl bisphenol A, epoxy equivalent: 185, produced by Asahi Chiba K.K.), 0.14 g of DMP-30 (2,4,6-tris (dimethylaminomethyl)phenol, produced by Wako Pure Chemical Industries, Ltd.) and 5 mg of hydroquinone monomethyl ether were charged. Under a nitrogen stream, the reaction mixture was heated to 100° C. in an oil bath while stirring with a magnetic stirrer. After 10 hours, the heating was stopped and the flask was cooled. The obtained reaction mixture was analyzed by a high-performance liquid chromatograph, as a result, 0.43 g of the raw material methacrylic acid remained and the conversion of methacrylic acid was 95.0%. This reaction product was designated as "Sample Q".

Curing Test 1 (catalyst-free heat curing)

A few droplets of each of Samples A, B, C, D, E, F, G, H, I, J, K, L, M, P and Q were dropped on a glass plate by means of a syringe and heated in a gear oven (Perfect Oven PV-110, manufactured by TABAI ESPEC K.K.) for 1 hour with an attempt to perform catalyst-free heat curing. The results are shown in Table 1.

TABLE 1

|  | Curing Test 1 |
| --- | --- |
| Sample A | ○ |
| Sample B | ○ |
| Sample C | ○ |
| Sample D | ○ |
| Sample E | ○ |
| Sample F | ○ |
| Sample G | ○ |
| Sample H | ○ |
| Sample I | ○ |
| Sample J | ○ |
| Sample K | ○ |
| Sample L | ○ |
| Sample M | ○ |
| Sample P | X |
| Sample Q | X |

○: cured, X: not cured

Test Using Coating to PET

Samples A, B, E, F, G and H, pentaerythritol triacrylate (hereinafter referred to as "PETA") and pentaerythritol tetracrylate (hereinafter referred to as "PETEA") were each weighed to 1 g and diluted with toluene to have a toluene content of 50 mass %. To this mixture, Irgacure (registered trademark) 184 (1-hydroxycyclohexylphenyl ketone, produced by Ciba Specialty Chemicals) was added and dissolved to 5 mass % based on each samples. A few droplets of each toluene solution were dropped on a glass plate by means of a syringe and cured using an ultraviolet ray irradiation apparatus TOSCURE 401 (manufactured by Toshiba K.K.). The UV irradiation was continued until the sample was not peeled by scratching with a finger to obtain a cured product sample. The cured product samples were subject to the tests as listed in Table 2 below.

The results are shown in Table 2.

the conditions of 100° C. for 0.5 hour plus 130° C. for 1 hour plus 160° C. for 1 hour. The liquid containing the mixture of VE resin and styrene was cured under the conditions of 130° C. for 1 hour plus 160° C. for 1 hour.

TABLE 2

| | Test method | Flexing resistance mmφ | Taber abrasion shaving amount (mg) 0.5 kg - 500 rotations | Erichsen value rupture length mm | Stress at film rupture tencile stress MPa | elongation % | Adhesion test cross-cut cross-cut test | tape peeling test | UV curing time under nitrogen atmosphere(s) | under oxygen atmosphere(s) |
|---|---|---|---|---|---|---|---|---|---|---|
| Sample A | JIS K 5400 | 2> | 7 (0.6) | 9.2 | 135 | 33 | 10 | 8 | 60 | 90 |
| Sample B | JIS K 5400 | 2> | 29 (7.7) | 6.5 | 110 | 17 | 10 | 0 | 65 | — |
| Sample E | JIS K 5400 | 2> | 11 (1.0) | 7.6 | 129 | 26 | 10 | 8 | 45 | 90 |
| Sampel F | JIS K 5400 | 2> | 13 (1.2) | 9.1 | 146 | 47 | 10 | 4 | 60 | 35 |
| Sample G | JIS K 5400 | 3 | 18 (2.1) | 9.9 | 128 | 25 | 10 | 8 | 90 | 120 |
| Sample H | JIS K 5400 | 2> | 12 (0.8) | 14.2 | 176 | 75 | 10 | 10 | 15 | 10 |
| PETA | JIS K 5400 | 6 | 24 | 3.2 | 8.9 | 3.7 | 4 | 0 | 15 | — |
| PETEA | JIS K 5400 | 4 | 12 | 3.3 | 8.2 | 2.2 | 2 | 0 | 15 | — |

From the results in Table 2, it is proved that the compounds according to the present invention exhibit good adhesion to a PET film and form a film having good tensile strength and elongation.

Test for Cast Molded Product

Dicumyl peroxide was dissolved in each of Samples A, B, C and D and a mixture of a vinylester (VE) resin (tradename: Ripoxy VR-77, manufactured by Showa Highpolymer K.K.) and styrene of a mass ratio of 70:30 in an amount of 2 mass % based on each resin, and the mixtures were each cast into a die made of PET and having a thickness of 4 mm. Then, the mixtures containing Samples A to D were cured under Further, dicumyl peroxide was dissolved in an unsaturated polyester (UP) resin (tradename: Upika 6424, produced Nippon Upika K.K.) in an amount of 2 mass % based on the resin, and the mixture was cast into a die made of glass having a thickness of 4 mm. Then, the mixture was cured under the conditions of 60° C. for 1 hour plus 160° C. for 1 hour.

The obtained cured products were subjected to exaluation of mechanical properties, thermal properties, electrical properties, optical properties, etc. The results are shown in Table 3 below.

TABLE 3

| | Test method | Sample A | Sample B | Sample C | Sample D | UP resin | VE resin + styrene |
|---|---|---|---|---|---|---|---|
| Mechanical properties | | | | | | | |
| Flexural strength (MPa) 23° C. | JIS K 7203 | 79 | 54 | 69 | 75 | 112 | 133 |
| Flexural modulus (MPa) 23° C. | JIS K 7203 | 3370 | 2550 | 2850 | 2990 | 3800 | 3380 |
| Tensile strength (MPa) | JIS K 7203 | 36 | 34 | 38 | 51 | 73 | 80 |
| Charpy impact value (kJ/m$^2$) | JIS K 7111 | 1.4 | 1.6 | 1.4 | 1.8 | 0.9 | 1.1 |
| Tensile sheer adhesion strength (kg/cm$^2$) 23° C. | JIS K 6850 | 48 | 27 | 62 | 14 | 28 | 35 |
| Thermal properties | | | | | | | |
| HDT (° C.) 18.5 kg/cm | JIS K 7207 | 178 | 133 | 110 | 85 | 119 | 97 |
| Tg (° C.) | JIS K 7197 | 103 | 45 | 62 | 48 [80] | 113 | 88 |
| Electrical properties | | | | | | | |
| Volume resistivity (Ω · cm) 23° C. | JIS K 6911 | $7 \times 10^{14}$ | $3 \times 10^{13}$ | $4 \times 10^{14}$ | $2 \times 10^{14}$ | $6 \times 10^{15}$ | $4 \times 10^{14}$ |
| Dielectric constant 1 MHz | JIS K 6760 | 3.8 | 4.1 | 3.6 | 3.9 | 2.9 | 3.6 |
| Dielectric dissipation factor 1 MHz | JIS K 6760 | 0.038 | 0.051 | 0.038 | 0.041 | 0.012 | 0.029 |
| Optical properties | | | | | | | |
| Refractive index | ASTM D542 | 1.559 | 1.522 | 1.523 | 1.530 | 1.562 | 1.577 |
| Abbe number | | 39 | 53 | 45 | 49 | 33 | 33 |
| Other properties | | | | | | | |
| Barcol hardness (934-1 Type) | JIS K 6911 | 50 | 46 | 43 | 43 | 49 | 49 |

TABLE 3-continued

| | Test method | Sample A | Sample B | Sample C | Sample D | UP resin | VE resin + styrene |
|---|---|---|---|---|---|---|---|
| Pencil hardness | JIS K 5400 | 5H | 6H | 4H–5H | 5H | — | — |
| Specific gravity | JIS K 7112 | 1.27 | 1.31 | 1.23 | 1.27 | 1.19 | 1.19 |
| Volume shrinkage (%) | | 5.4 | 8.3 | 5.8 | 6.8 | 7.7 | 7.9 |

From the results in Table 3, it is proved that the cured products according to the present invention have excellent mechanical properties, particularly excellent impact resistance.

Test for Cast Molded Product

Dicumyl peroxide was dissolved in each of Samples K, L and M in an amount of 2 mass % based on each resin, and the mixtures were each cast into a die made of glass and having a thickness of 4 mm. Then, the mixtures were cured under the conditions of 120° C. for 5 hours plus 130° C. for 5 hours plus 140° C. for 5 hours plus 150° C. for 5 hours plus 160° C. for 2 hours.

The obtained cured products of Samples K, L and M were cut into a test piece of a size of 10 mm×10 mm×4 mm and 5 pieces for each product were each introduced in a 300 ml egg-plant type flask equipped with a reflux condenser. Then, 150 ml of chloroform was introduced into the flask and heated and refluxed for 3 hours. Then, the mixture was cooled and analyzed for the presence or absence of the catalyst extracted into chloroform by gel permeation chromatography (column: F801, manufactured by Showa Denko K.K., eluent: chloroform, detector: RI detector). The catalyst was not detected from the chloroform used for the extraction of each of the test pieces of the cured products of Samples K and L but, the catalyst, 2,4,6-tris(dimethylaminomethyl) phenol, was detected from the chloroform used for the extraction of the test piece of the cured product of Samples M.

From the above results, it is proved that a polymerizable composition is produced by using a catalyst having a radical polymerization functional group, the catalyst does not ooze out from a cured product obtained by curing the polymerizable composition.

Industrial Applicability

According to the present invention, a polymerizable compound exhibiting a good adhesive property to a substrate such as of PET and imparted with radical polymerizability to enable heat curing and/or active energy ray curing can be provided, and also a production process of the polymerizable compound, a composition using the polymerizable compound, a cured product obtained by curing the composition and a production process of the cured product can be provided.

What is claimed is:

1. A polymerizable compound represented by the following formula (1):

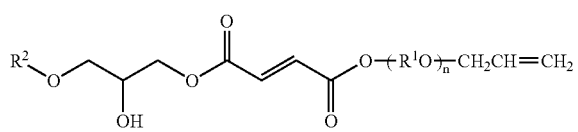
(1)

wherein each $R^1$ independently represents at least one organic residue selected from the group consisting of alkylene groups, branched alkylene groups, cycloalkylene groups and arylene groups, $R^2$ represents an organic residue derived from an alcohol compound, a phenol compound or a carboxylic acid compound, n represents an integer of 1 to 20, and $R^2$ may further contain a group represented by the following formula (2) and/or formula (3):

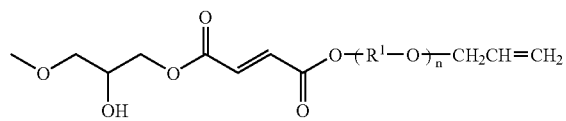
(2)

wherein $R^1$ and n are as defined above;

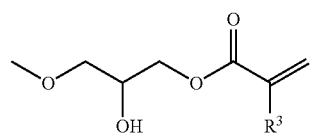
(3)

wherein $R^3$ represents H or $CH_3$.

2. A compound according to claim 1, wherein each $R^1$ is independently at least one member selected from the organic residues represented by the following structural formulae (6) to (12):

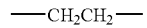
(6)

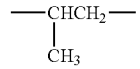
(7)

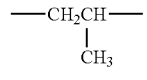
(8)

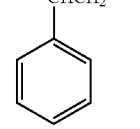
(9)

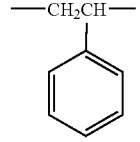
(10)

-continued

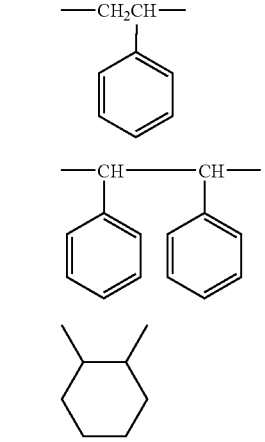
(10)

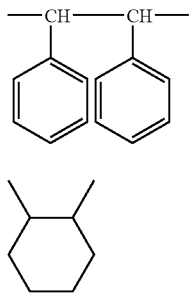
(11)

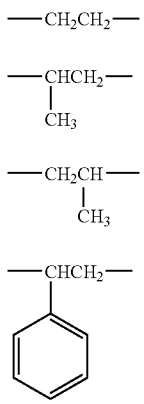
(12)

3. A compound according to claim 1 or 2, wherein $R^2$ is an organic residue derived from a compound selected from the group consisting of ethylene glycol, propylene glycol, 1,3-propanediol, 1,4-butanediol, 1,6-hexanediol, neopentyl glycol, glycerin, trimethylolethane, trimethylolpropane, 1,4-cyclohexanediol, 1,4-cyclohexanedimethanol, bisphenol A, bisphenol A propylene oxide adduct, bisphenol A ethylene oxide adduct, brominated bisphenol A, hydrogenated bisphenol A, bisphenol F, phenol novolak resin, cresol novolak resin, 1,2-cyclohexanedicarboxylic acid, 1,3-cyclohexanedicarboxylic acid, 1,4-cyclohexanedicarboxylic acid, 1,3-cyclohexene-1,2-dicarboxylic acid, phthalic acid, isophthalic acid and terephthalic acid.

4. A compound according to claim 1 or 2, wherein each $R^1$ is independently at least one member selected from the organic residues represented by the following structural formulae (6) to (12), and $R^2$ is an organic residue derived from a compound selected from the group consisting of ethylene glycol, propylene glycol, 1,3-propanediol, 1,4-butanediol, 1,6-hexanediol, neopentyl glycol, glycerin, trimethylolethane, trimethylolpropane, 1,4-cyclohexanediol, 1,4-cyclohexanedimethanol, bisphenol A, bisphenol A propylene oxide adduct, bisphenol A ethylene oxide adduct, brominated bisphenol A, hydrogenated bisphenol A, bisphenol F, phenol novolak resin, cresol novolak resin, 1,2-cyclohexane-dicarboxylic acid, 1,3-cyclohexanedicarboxylic acid, 1,4-cyclohexanedicarboxylic acid, 3-cyclohexene-1,2-dicarboxylic acid, phthalic acid, isophthalic acid and terephthalic acid:

—CH₂CH₂— (6)

—CHCH₂— 
   |
   CH₃ (7)

—CH₂CH— 
     |
     CH₃ (8)

—CHCH₂— (9)

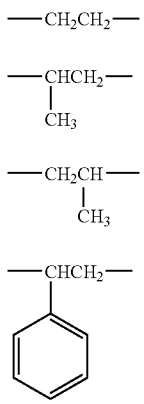

5. A process for producing a polymerizable compound as set forth in claim 1, comprising:
a step of performing an addition reaction between at least one compound selected from the compounds represented by the following formula (4) and at least one compound selected from the compounds represented by the following formula (5) in the presence of a catalyst to obtain a polymerizable compound:

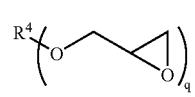
(4)

wherein $R^4$ represents an organic residue derived from an alcohol compound, a phenol compound or a carboxylic acid compound, and q represents an integer of 1 or more;

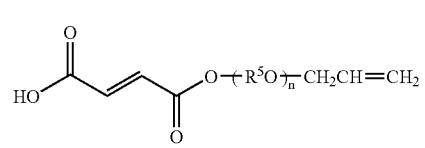
(5)

wherein $R^5$ represents at least one member selected from an alkylene group, a branched alkylene group, a cycloalkylene group and an arylene group, and n represents an integer of 1 to 20.

6. A process for producing a polymerizable compound represented by the following (1)

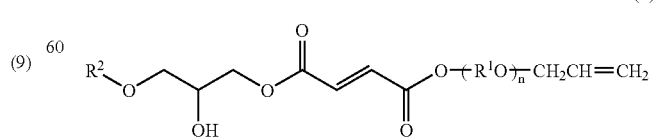
(1)

wherein each $R^1$ independently represents at least one organic residue selected from the group consisting of alkylene groups, branched alkylene groups, cycloalkylene groups and arylene groups, R² represents an organic residue derived from an alcohol compound, a phenol compound or a carboxylic acid compound, n represents an integer of 0 to 20, and R² may further contain a group represented by the following formula (2) and/or formula (3):

(2)

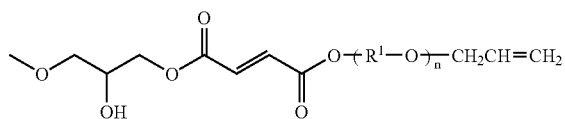

wherein R¹ and n are as defined above;

(3)

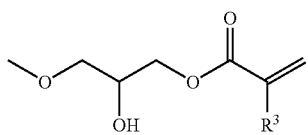

wherein R³ represents H or CH₃, comprising:
a step of performing an addition reaction between at least one compound selected from the compounds represented by the following formula (4), at least one compound selected from the compounds represented by the following formula (5) and at least one compound selected from the compounds represented by the following formula (13) in the presence of a catalyst to obtain a polymerizable compound:

(4)

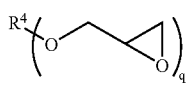

wherein R⁴ represents an organic residue derived from an alcohol compound, a phenol compound or a carboxylic acid compound, and q represents an integer of 1 or more;

(5)

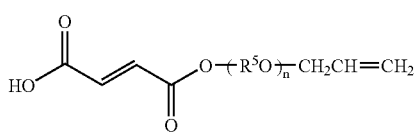

wherein R⁵ represents at least one member selected from an alkylene group, a branched alkylene group, a cycloalkylene group and an arylene group, and n represents an integer of 0 to 20;

(13)

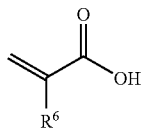

wherein R⁶ represents H or CH₃.

7. A process according to claim 5 or 6, wherein R⁴ is at least one organic residue derived from ethylene glycol, propylene glycol, 1,3-propanediol, 1,4-butanediol, 1,6-hexanediol, neopentyl glycol, glycerin, trimethylolethane, trimethylolpropane, 1,4-cyclohexanediol, 1,4-cyclohexanedimethanol, bisphenol A, bisphenol A propylene oxide adduct, bisphenol A ethylene oxide adduct, brominated bisphenol A, hydrogenated bisphenol A, bisphenol F, phenol novolak resin, cresol novolak resin, 1,2-cyclohexanedicarboxylic acid, 1,3-cyclohexanedicarboxylic acid, 1,4-cyclohexanedicarboxylic acid, 3-cyclohexene-1,2-dicarboxylic acid, phthalic acid, isophthalic acid and terephthalic acid.

8. A process according to claim 5 or 6, wherein each R⁵ is independently at least one member selected from the organic residues represented by the following structural formulae (6) to (12):

(6)
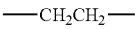

(7)
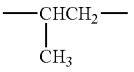

(8)
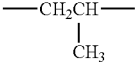

(9)
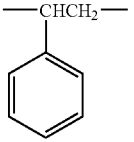

(10)
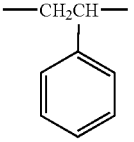

(11)
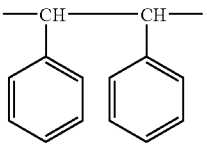

(12)
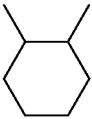

9. A process according to claim 5 or 6, wherein the catalyst is at least one member selected from the group consisting of metal halides, pyridine compounds, pyridinium salts, tertiary amines, quaternary ammonium salts, phosphine compounds and phosphonium salts.

10. A process according to claim 9, wherein the catalyst is at least one member selected from the group consisting of tin chloride, pyridine, isoquinoline, quinoline, 2,4,6-tris (dimethylaminomethyl)-phenol, triethylamine, triphenylphosphine, benzyltrimethylammonium salts, benzyltriethylammonium salts, ethyltriphenylphosphonium salts, tetraphenylphosphonium salts and benzyltriphenylphosphonium salts.

11. A process according to claim 5 or 6, wherein the catalyst is a catalyst having a radical polymerization-functional group.

12. A process according to claim 11, wherein the catalyst is at least one member selected from the group consisting of 2-vinylpyridine, 3-vinylpyridine, 4-vinylpyridine, N,N-dimethylaminoethyl ethacrylate, N,N-dimethylaminoethyl acrylate, N-(3-N',N'-dimethylaminopropyl)-acrylamide, N-(3-N',N'-dimethylaminopropyl)-methacrylamide, trimethylmethacryloyloxyethylammonium salts, trimethylacryloyloxyethylammonium salts, trimethylacryloylaminopropylammonium salts, trimethylmethacryloylaminopropylammonium salts and dimethyldiallylammonium salts.

13. A polymerizable composition comprising at least one polymerizable compound as set forth in claim 1 as an essential component.

14. A composition according to claim 13, which contains from 0.1 to 10 parts by mass of at least one radical polymerization initiator per 100 parts by mass of all curable components in the polymerizable composition.

15. A cured product obtained by curing a polymerizable composition as set forth in claim 13.

16. A process for producing a cured product comprising curing a polymerizable composition as set forth in claim 13.

17. A process according to claim 16, wherein the polymerization composition is heat cured or cured by an active energy.

* * * * *